United States Patent
Suzuki et al.

(10) Patent No.: US 11,241,475 B2
(45) Date of Patent: Feb. 8, 2022

(54) PREVENTIVE AND/OR THERAPEUTIC AGENT FOR OSTEOGENESIS IMPERFECTA AND OTHER DISEASES

(71) Applicant: Pharma Foods International Co., Ltd., Kyoto (JP)

(72) Inventors: Chihiro Suzuki, Kyoto (JP); Utano Nakamura, Kyoto (JP); Mujo Kim, Kyoto (JP)

(73) Assignee: Pharma Foods International Co., Ltd., Kyoto (JP)

( * ) Notice: Subject to any disclaimer, the term of this patent is extended or adjusted under 35 U.S.C. 154(b) by 145 days.

(21) Appl. No.: 16/306,419

(22) PCT Filed: Jun. 27, 2017

(86) PCT No.: PCT/JP2017/023633
§ 371 (c)(1),
(2) Date: Nov. 30, 2018

(87) PCT Pub. No.: WO2018/003817
PCT Pub. Date: Jan. 4, 2018

(65) Prior Publication Data
US 2020/0316161 A1　Oct. 8, 2020

(30) Foreign Application Priority Data
Jun. 27, 2016　(JP) ............... JP2016-127102

(51) Int. Cl.
| A61K 38/07 | (2006.01) |
| A61K 38/04 | (2006.01) |
| C07K 5/00 | (2006.01) |
| C07K 5/04 | (2006.01) |
| C07K 5/10 | (2006.01) |
| A61P 19/08 | (2006.01) |
| A61P 19/02 | (2006.01) |
| A61K 38/08 | (2019.01) |
| A61K 9/00 | (2006.01) |

(52) U.S. Cl.
CPC ............ *A61K 38/08* (2013.01); *A61K 9/0053* (2013.01); *A61K 38/04* (2013.01); *A61K 38/07* (2013.01); *A61P 19/02* (2018.01); *A61P 19/08* (2018.01); *C07K 5/00* (2013.01); *C07K 5/04* (2013.01); *C07K 5/10* (2013.01)

(58) Field of Classification Search
CPC ........ A61K 38/07; A61K 38/08; A61K 38/04; C07K 5/10; C07K 7/06; C07K 5/00; C07K 5/04; A61P 19/08; A61P 19/02
See application file for complete search history.

(56) References Cited

U.S. PATENT DOCUMENTS

2015/0164973 A1　6/2015　Kim et al.
2016/0362466 A1*　12/2016　Yamazaki ................ C07K 7/06

FOREIGN PATENT DOCUMENTS

| JP | 4-53471 A | 2/1992 |
| WO | WO 2006/075558 A1 | 7/2006 |
| WO | WO 2014/007318 A1 | 1/2014 |
| WO | WO 2015/129726 A1 | 9/2015 |
| WO | WO-2015129726 A1 * | 9/2015 ............... A61K 8/64 |

OTHER PUBLICATIONS

Rauch et al., Lancet, 2004, vol. 363: 1377-1385.*
International Search Report for PCT/JP2017/023633 dated Oct. 3, 2017.

* cited by examiner

*Primary Examiner* — Xiaozhen Xie
(74) *Attorney, Agent, or Firm* — Knobbe, Martens, Olson & Bear, LLP

(57) ABSTRACT

Provided is an agent for preventing and/or treating osteogenesis imperfecta, osteoporosis and/or osteoarthritis, the agent comprising a peptide consisting of one of the following amino acid sequences: (a) Val-Asn-Pro-Glu-Ser-Glu-Glu-Glu (SEQ ID NO: 1) and (b) Val-Asn-Pro-Glu (SEQ ID NO: 2). The agent of the present invention can be orally ingested, has osteogenic function, and has a preventive and/or healing-promoting effect on bone fractures and is therefore very useful for prevention and/or treatment of osteogenesis imperfecta, osteoporosis and/or osteoarthritis.

10 Claims, 19 Drawing Sheets
Specification includes a Sequence Listing.

No.1: 100 mg/kg/day (p.o)
hGH: 500 μg/kg/day (s.c)

TC: Tetracycline (fluorescent label)
CL: Calcein (fluorescent label)

TC: Tetracycline (fluorescent label)
CL: Calcein (fluorescent label)

No.1: 1,5,10 mg/kg (p.o)
No.2: 0.1,1,10 mg/kg (p.o)

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial
<220> FEATURE:
<223> OTHER INFORMATION: Synthetic peptide

<400> SEQUENCE: 1

Val Asn Pro Glu Ser Glu Glu Glu
1               5

<210> SEQ ID NO 2
<211> LENGTH: 4
<212> TYPE: PRT
<213> ORGANISM: Artificial
<220> FEATURE:
```

```
<223> OTHER INFORMATION: Synthetic peptide

<400> SEQUENCE: 2

Val Asn Pro Glu
1

<210> SEQ ID NO 3
<211> LENGTH: 4
<212> TYPE: PRT
<213> ORGANISM: Artificial
<220> FEATURE:
<223> OTHER INFORMATION: Synthetic peptide

<400> SEQUENCE: 3

Glu Pro Asn Val
1
```

PREVENTIVE AND/OR THERAPEUTIC AGENT FOR OSTEOGENESIS IMPERFECTA AND OTHER DISEASES

CROSS REFERENCE TO RELATED APPLICATIONS

This application is a U.S. National Phase Application of PCT International Application Number PCT/JP2017/023633, filed on Jun. 27, 2017, designating the United States of America and published in the Japanese language, which is an International Application of and claims the benefit of priority to Japanese Patent Application No. 2016-127102, filed on Jun. 27, 2016. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-IWAT008-002APC.txt, the date of creation of the ASCII text file is Oct. 24, 2018, and the size of the ASCII text file is 1 KB.

TECHNICAL FIELD

The present invention relates to an agent for preventing and/or treating osteogenesis imperfecta and other diseases. In particular, the present invention relates to an agent for preventing and/or treating osteogenesis imperfecta, osteoporosis and/or osteoarthritis.

BACKGROUND ART

Osteogenesis imperfecta is a disease characterized by bone fragility and is caused by congenital defects in the synthesis of collagen, which is one of the principal components of bones. Typical symptoms are easily breakable bones, progressive bone deformity, etc. The disease occurs in one in approximately 20,000 people, and has been recognized as a rare and intractable disease. During the period of infancy and childhood, patients with osteogenesis imperfecta may experience multiple bone fractures, including frequent long bone fractures and continuous spinal compression fractures, and may also have severe bone deformity, resulting in inability to walk and other disabilities. Even after the patients reach the adulthood, they may require a wheelchair and/or nursing care (Non Patent Literature 1). Bisphosphonates have inhibitory effects on bone resorption and are only one therapeutic option that has been approved as effective for internal treatment of the disease in Japan. Cyclical intravenous administration of bisphosphonates has been proven effective for prevention of bone fractures. Their efficacy is known to be based on their ability to inhibit the activity of osteoclasts and thereby to suppress bone resorption. However, osteoclasts play an important role in the healing of bone fractures during the repair stage, and the inhibitory effects of bisphosphonates on the activity of osteoclasts may reduce the function of osteoclasts. If the patients already have a bone fracture, the administration of bisphosphonates has the risk of delaying the healing of the bone fracture, and is therefore contraindicated in osteogenesis imperfecta patients with bone fractures. Another problem of bisphosphonates is adverse effects, such as hypocalcemia, dyspnea, etc. Accordingly, there is a need for development of a novel osteogenesis-promoting agent that offers enhanced efficacy and safety in the treatment of osteogenesis imperfecta.

Bisphosphonates, based on the observation of the healing process of bone fractures in osteogenesis imperfecta, have also been reported to delay disappearance of fracture lines as compared with no use of bisphosphonates (Non Patent Literature 2). Microfractures occur even in normal bones and accumulation of microfractures is often observed in old bones. Administration of bisphosphonates induces osteopetrosis and increases fractures (Non Patent Literature 3). Bisphosphonates are known not to affect bone growth directly; however, bones grow while maintaining their shapes through continuous remodeling, and if bone remodeling is continuously suppressed by bisphosphonates, the risk of the malformation of bones may arise (Non Patent Literature 4). Accordingly, there is a need for a novel osteogenesis-promoting agent as a therapeutic drug for osteogenesis imperfecta that can promote osteogenesis through a novel mechanism of action without inhibiting the activity of osteoclasts, and thereby is capable of preventing bone fractures and promoting the healing of bone fractures. Most of osteogenesis imperfecta patients are infants and children, and accordingly a novel osteogenesis-promoting agent is also required to cause no growth abnormalities in patients and to be an orally available form that is easily taken.

During skeletal development, most of skeletal bones except the skull bones and the clavicles are formed through the process of endochondral ossification. In other words, each skeletal bone is first formed as cartilage. Then the chondrocytes in the center of the diaphysis of the cartilage hypertrophy, and enter into apoptosis. Osteoblasts and osteoclasts migrate from blood vessels into the central region, and the cartilage is replaced with bone tissue to form a bone (Non Patent Literature 5).

Similarly, during the repair stage in the healing process of bone fractures, mesenchymal stem cell-derived chondrocytes form cartilage around the fracture site and fill the fracture gap prior to fibrous callus formation through membranous ossification. The cartilage is then enlarged. After blood vessel penetration, the cartilage is calcified. The calcified cartilage is then absorbed by osteoclasts, and replaced by bone tissue produced by osteoblasts (endochondral ossification). In this manner, the cartilage produced after bone fractures is exclusively replaced with bone tissue, and the fibrous callus is replaced with the lamellar bone, leading to bone fusion (Non Patent Literature 6). The roles of various types of mesenchymal stem cell-derived cell populations, including chondrocytes, osteoblasts, osteoclasts, etc., in osteogenesis and healing of bone fractures have been gradually clarified.

Certain peptides are known to have a promoting activity on the proliferation of osteoblastic precursor cells (Patent Literature 1). However, the effect of the peptides on osteogenesis and fracture healing in skeletal diseases such as osteogenesis imperfecta is largely unknown. For treatment of osteoporosis and osteoarthritis, several medicinal drugs are currently available, but the efficacy is far from a satisfactory level. In these circumstances, the present invention provides a preventive and/or therapeutic drug for osteogenesis imperfecta, osteoporosis and osteoarthritis as described in detail below.

CITATION LIST

Patent Literature

Patent Literature 1: WO 2015/129726

Non Patent Literature

Non Patent Literature 1: Kotsukeiseifuzensho no Shinryo Guideline (the Committee on Pharmaceutical Affairs of the Japanese Society for Pediatric Endocrinology), The Journal of the Japan Pediatric Society. 2006; 110:1467-1471.
Non Patent Literature 2: Hiroyuki Tanaka (supervised by Yoshiki Seino: Hone no Byoki to Tsukiau niha, revised edition, Medical Review Co., Ltd.:198-199, 2010).
Non Patent Literature 3: Mashiba T, Hirano T, Turner C H, et al.: Suppressed bone turnover by bisphosphonates increases microdamage accumulation and reduces some biomechanical properties in dog rib. J Bone Miner Res 15:613-620, 2000.
Non Patent Literature 4: Whyte M P, Wenkert D, Clements K L, et al.: Bisphosphonate-induced osteopetrosis. N Engl J Med 349:457-463, 2003.
Non Patent Literature 5: Noriyuki Tsumaki, Hone/nankotsu no Saisei, Experimental medicine, Vol. 32, No. 7 (special issue), 177-184.
Non Patent Literature 6: Arata Nakajima et al., Recent progress in fracture healing research through molecular and cellular biology, Chiba Medical Journal 86:83-91, 2010.

SUMMARY OF INVENTION

Technical Problem

An object of the present invention is to provide a novel and effective agent for preventing and/or treating osteogenesis imperfecta, osteoporosis and/or osteoarthritis.

Solution to Problem

The inventors conducted extensive research and as a result found that peptides consisting of the amino acid sequences of SEQ ID NOs: 1 and 2 have a proliferation-promoting effect on chondrogenic cells and osteoblastic precursor cells as well as a promoting effect on IGF-1 (insulin-like growth factor) production. In connection with the above effects, oral administration of the peptide consisting of the amino acid sequence of SEQ ID NO: 1 to rats in the growth phase promotes osteogenesis in a dose-dependent manner, and also promotes the growth of the hypertrophic cartilage layer and the growth plate. The peptide was also found to promote the proliferation of osteoblastic precursor cells, bone calcification and bone volume increase in the secondary cancellous bone. Also found was that oral administration of the peptide consisting of the amino acid sequence of SEQ ID NO: 1 promotes long bone growth. These effects were also observed when the peptide consisting of the amino acid sequence of SEQ ID NO: 2 was administered.

The inventors also found the following. When orally administered, the peptide consisting of the amino acid sequence of SEQ ID NO: 1 is poorly digested by gastric juice, but is metabolized by intestinal juice into the peptide consisting of the amino acid sequence of SEQ ID NO: 2, which is then absorbed through the intestinal mucosa. The peptide consisting of the amino acid sequence of SEQ ID NO: 2, when orally administered, is not decomposed any further in the stomach and intestines, and is absorbed through the intestinal mucosa into the body. The peptide consisting of the amino acid sequence of SEQ ID NO: 2 that has been absorbed into the body promotes the proliferation of mesenchymal stem cell-derived chondrocytes, which undergo endochondral ossification, and then the peptide promotes the proliferation of osteoblasts, thereby promoting osteogenesis and fracture healing. The peptide consisting of the amino acid sequence of SEQ ID NO: 2, when orally administered, also promotes the production of IGF-1 in the liver. The produced IGF-1 not only promotes osteogenesis and fracture healing but also promotes bone growth together with the peptide consisting of the amino acid sequence of SEQ ID NO: 2. Therefore, the peptides consisting of the amino acid sequences of SEQ ID NOs: 1 and 2 are found to be useful as novel oral drugs capable of preventing bone fractures and promoting fracture healing in osteogenesis imperfecta through a novel mechanism of action without inhibiting the activity of osteoclasts, which inhibition is unavoidable in the use of the currently available therapeutic drugs bisphosphonates. The present invention will effectively contribute to treatment of osteogenesis imperfecta by serving as the world's first "oral available drug for osteogenesis imperfecta having promoting effects on fracture healing and long bone growth".

Patent Literature 1, supra, discloses, as preferred embodiments, a pentapeptide, a heptapeptide, an octapeptide and a pentadecapeptide each having a specific sequence. According to the present invention, the peptides consisting of the amino acid sequences of SEQ ID NOs: 1 and 2 unexpectedly exhibit significant effects not only on osteogenesis imperfecta but also on the promotion of the healing of bone fractures. Of these peptides, the peptide consisting of the amino acid sequence of SEQ ID NO: 2 is distinguished over those specifically disclosed in Patent Literature 1, and has advantages of being able to be efficiently synthesized due to its simple structure and being able to be efficiently absorbed into the body. The peptide consisting of the amino acid sequence of SEQ ID NO: 2 also has advantages over the peptide consisting of the amino acid sequence of SEQ ID NO: 1 in that it has higher effects per unit mass and thus the size of the dosage form can be conveniently reduced.

That is, the present invention includes the following.
(1) An agent for preventing and/or treating osteogenesis imperfecta, the agent comprising a peptide consisting of one of the following amino acid sequences: (a) Val-Asn-Pro-Glu-Ser-Glu-Glu-Glu (SEQ ID NO: 1) and (b) Val-Asn-Pro-Glu (SEQ ID NO: 2).
(2) An agent for preventing and/or treating osteoporosis, the agent comprising a peptide consisting of one of the following amino acid sequences: (a) Val-Asn-Pro-Glu-Ser-Glu-Glu-Glu (SEQ ID NO: 1) and (b) Val-Asn-Pro-Glu (SEQ ID NO: 2).
(3) An agent for preventing and/or treating osteoarthritis, the agent comprising a peptide consisting of one of the following amino acid sequences: (a) Val-Asn-Pro-Glu-Ser-Glu-Glu-Glu (SEQ ID NO: 1) and (b) Val-Asn-Pro-Glu (SEQ ID NO: 2).
(4) The agent according to any one of the above (1) to (3), which is an agent for preventing a bone fracture and/or promoting the healing of a bone fracture.
(5) The agent according to any one of the above (1) to (4), which is for oral administration.

(6) A medicament for preventing and/or treating osteogenesis imperfecta, osteoporosis and/or osteoarthritis, the medicament comprising the agent according to any one of the above (1) to (5).
(7) The agent or medicament according to any one of the above (1) to (6), which promotes osteogenesis.
(8) A combination comprising the agent or medicament according to any one of the above (1) to (6) and another medicament for preventing and/or treating osteogenesis imperfecta, osteoporosis and/or osteoarthritis.

The present invention also includes the following aspects.
(9) The agent according to any one of the above (1) to (3), which comprises, as an active ingredient, the peptide consisting of the amino acid sequence (b) Val-Asn-Pro-Glu (SEQ ID NO: 2).
(10) The agent according to the above (9), which is for preventing a bone fracture and/or promoting the healing of a bone fracture.
(11) A pharmaceutical composition for preventing and/or treating osteogenesis imperfecta, osteoporosis and/or osteoarthritis, the composition comprising the peptide according to any one of the above (1) to (3), wherein the composition is administered simultaneously or sequentially with a compound having an inhibitory effect on osteoclasts or with a bisphosphonate.
(12) A pharmaceutical composition for a patient undergoing therapy with a compound having an inhibitory effect on osteoclasts or with a bisphosphonate, the composition comprising, as an active ingredient, the peptide according to any one of the above (1) to (3).

Advantageous Effects of Invention

The present invention provides a novel agent for preventing and/or treating osteogenesis imperfecta, osteoporosis and/or osteoarthritis. The agent can be orally available. The agent has osteogenic function. The agent has the effects of preventing bone fractures and/or promoting the healing of bone fractures. The agent is particularly advantageous in that it does not inhibit the activity of osteoclasts and that it has few adverse effects, for example, it does not cause hypocalcemia etc.

DESCRIPTION OF EMBODIMENTS

Peptides

Figure 1:
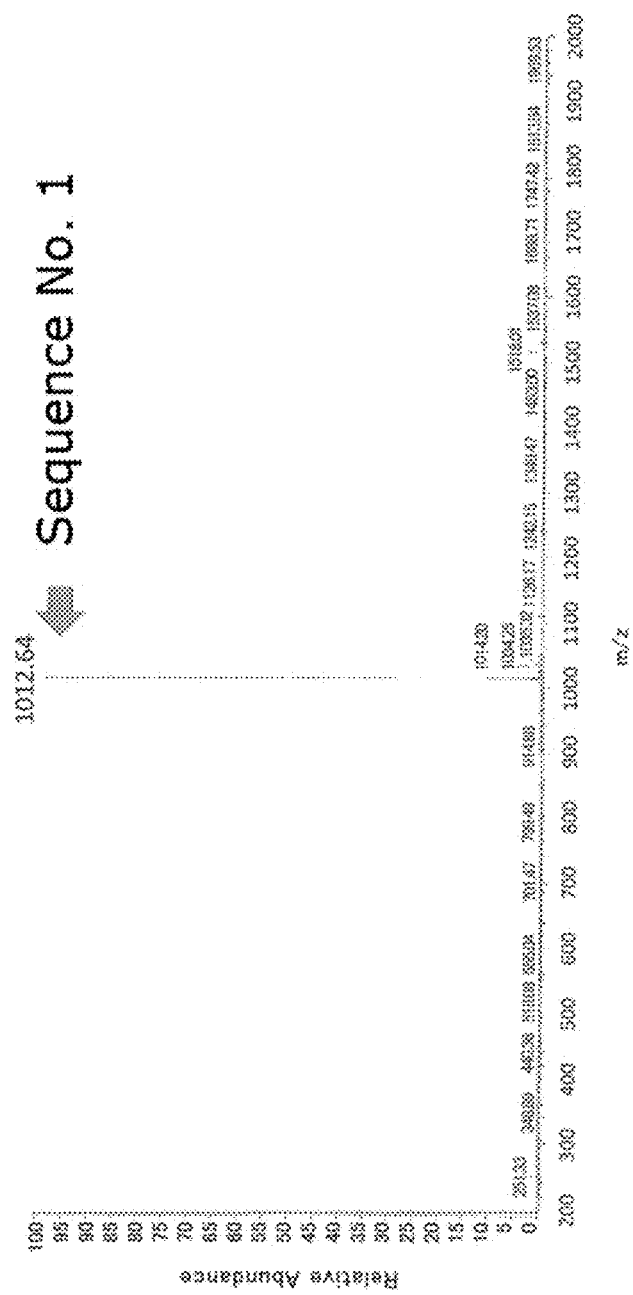
FIG. 1 is a graph showing the analysis results of a synthetic peptide (No. 1).

The present invention provides an agent for preventing and/or treating osteogenesis imperfecta, osteoporosis and/or osteoarthritis, the agent comprising, as an active ingredient, a peptide consisting of one of the following amino acid sequences: (a) Val-Asn-Pro-Glu-Ser-Glu-Glu-Glu (SEQ ID NO: 1) and (b) Val-Asn-Pro-Glu (SEQ ID NO: 2).

The peptide of the present invention consisting of one of the following amino acid sequences: (a) Val-Asn-Pro-Glu-Ser-Glu-Glu-Glu (SEQ ID NO: 1) and (b) Val-Asn-Pro-Glu (SEQ ID NO: 2) includes a derivative thereof and a pharmacologically acceptable salt thereof. The peptides consisting of the amino acid sequences of SEQ ID NOs: 1 and 2 are sometimes called in short herein the synthetic peptide No. 1 and the synthetic peptide No. 2, respectively.

A derivative of the peptide of the present invention may be a peptide whose amino acid sequence is as specified above and whose C-terminus may be a carboxyl group (—COOH), a carboxylate (—COO⁻), an amide (—CONH$_2$) or an ester (—COOR). Examples of R in the ester include $C_{1-6}$ alkyl groups such as methyl, ethyl, n-propyl, isopropyl and n-butyl; $C_{3-8}$ cycloalkyl groups such as cyclopentyl and cyclohexyl; $C_{6-12}$ aryl groups such as phenyl and α-naphthyl; $C_{7-14}$ aralkyl groups such as phenyl-$C_{1-2}$ alkyl groups, e.g., benzyl and phenethyl, and α-naphthyl-$C_{1-2}$ alkyl groups, e.g., α-naphthylmethyl; and a pivaloyloxymethyl group, which is commonly used as an ester for oral administration. The amide form may be an amide; an amide substituted with one or two $C_{1-6}$ alkyl groups; an amide substituted with one or two $C_{1-6}$ alkyl groups substituted with a phenyl group; a substituted amide in which the nitrogen atom of the amide group and two adjacent substituents bound to the nitrogen atom form a 5- to 7-membered azacycloalkyl moiety, such as morpholino and piperidino; or the like.

The derivative of the peptide of the present invention also includes the peptide of the present invention in which the N-terminal amino group is protected with a protecting group (e.g., a $C_{1-6}$ acyl group such as a formyl group and a $C_{2-6}$ alkanoyl group, e.g., acetyl), the peptide of the present invention in which the N-terminal glutamyl residue arising from in vivo cleavage is pyroglutamated, and the peptide of the present invention in which a substituent (e.g., —OH, —SH, an amino group, an imidazole group, an indole group, or a guanidino group) on an amino acid side chain in the molecule is protected with a suitable protecting group (e.g., a $C_{1-6}$ acyl group such as a formyl group and a $C_{2-6}$ alkanoyl group, e.g., acetyl).

The side chains of the amino acids constituting the derivative of the peptide of the present invention may be substituted with a substituent. Examples of the substituent include, but are not limited to, a fluorine atom, a chlorine atom, a cyano group, a hydroxy group, a nitro group, an alkyl group, a cycloalkyl group, an alkoxy group, an amino group, and a phosphate group. Substituents on the side chains may be protected with a protecting group. The knowledge on suitable substituents, protecting groups, etc. is well established in the art, and such substituents, protecting groups, etc. may be used in the present invention.

The peptide of the present invention may form a salt. The salt is preferably physiologically acceptable. Examples of the physiologically acceptable salt include salts with acids, such as hydrochloric acid, sulfuric acid, phosphoric acid, lactic acid, tartaric acid, maleic acid, fumaric acid, oxalic acid, malic acid, citric acid, oleic acid, and palmitic acid; salts with hydroxides or carbonates of an alkali metal, such as sodium, potassium and calcium; salts with hydroxides or carbonates of an alkaline earth metal; salts with aluminum hydroxide or carbonate; and salts with triethylamine, benzylamine, diethanolamine, t-butylamine, dicyclohexylamine, arginine, etc.

The peptide of the present invention may contain a D-amino acid or a non-naturally occurring amino acid to the extent that the peptide retains its original characteristics. The peptide of the present invention or a derivative thereof may contain another substance linked thereto to the extent that the peptide or derivative retains its original characteristics. Examples of the substance linkable to the peptide include other peptides, lipids, sugars, sugar chains, an acetyl group, and naturally occurring or synthetic polymers. The peptide of the present invention may be subjected to modification such as glycosylation, side-chain oxidation, and phosphorylation to the extent that the resulting modified peptide retains the characteristics of the original peptide. The serine in the peptide of the present invention may be phosphorylated.

That is, the present invention includes a compound that is a derivative (or a modified form) of the peptides of SEQ ID NOs: 1 and 2 and shows the same physiological activity as that of the peptides of SEQ ID NOs: 1 and 2 (i.e., the osteogenic effect or the promoting effect on fracture healing as described later).

The peptide of the present invention can easily be produced by solid-phase synthesis (the Fmoc or Boc method) or liquid-phase synthesis in accordance with a known standard peptide synthesis protocol. Alternatively, the peptide of the present invention, a derivative thereof or a salt thereof can be produced by using a transformant carrying an expression vector containing a DNA encoding the peptide of the present invention, a derivative thereof or a salt thereof. Alternatively, the peptide of the present invention, a derivative thereof or a salt thereof can be produced by preparing a peptide using a transformant carrying an expression vector containing a DNA encoding a peptide containing the peptide of the present invention, a derivative thereof or a salt thereof, and cleaving the resulting peptide with a suitable protease or peptidase. Alternatively, the peptide of the present invention, a derivative thereof or a salt thereof can be produced by a method using an in vitro transcription-translation system. A wide variety of peptide derivatives and modified forms that maintain the physiology activity of the original peptide are conventionally known in the art, and such derivatives and modified forms may be used in the present invention.

The peptide of the present invention can be obtained by purifying a hydrolysate of chicken egg yolk proteins. The preparation method of a hydrolysate of egg yolk proteins and the purification method of the peptide are not particularly limited, and the preparation and purification may be done by a known method selected as appropriate. Specifically, the peptide can be obtained by, for example, preparing a defatted egg yolk powder, then preparing a hydrolysate from the powder using an enzyme such as a protease, and purifying a peptide of interest from the hydrolysate by ultrafiltration or chromatography such as HPLC.

Application for Prevention and/or Treatment of Osteogenesis Imperfecta, Osteoporosis and/or Osteoarthritis The peptide of the present invention exhibits the effects of preventing and/or treating osteogenesis imperfecta, osteoporosis and/or osteoarthritis. These effects herein are based on the same mechanism of action.

The effects of preventing and/or treating osteogenesis imperfecta, osteoporosis and/or osteoarthritis can be confirmed by the presence of an osteogenic effect and a promoting effect on fracture healing. In particular, the effects of preventing and/or treating osteogenesis imperfecta, osteoporosis and/or osteoarthritis can be confirmed by, for example, the promotion of long bone growth, an increase in the area of the hypertrophic cartilage layer and in the thickness of the growth plate, etc., an increase in the calcification rate and the bone volume in the secondary cancellous bone, the promotion of osteoblastic precursor cell proliferation, the promotion of chondrogenic cell proliferation, the promotion of IGF-1 production, etc. (see Examples). The term "growth plate" as used herein refers to, for example, the growing zone of a bone in the epiphysis. The term "secondary cancellous bone" as used herein refers to, for example, mature cancellous bone. The peptide of the present invention is particularly advantageous in that it has a promoting effect on long bone growth as well as a promoting effect on fracture healing.

It should be noted that the peptide of the present invention is particularly advantageous in that it does not inhibit the activity of osteoclasts and that it has few adverse effects, for example, it does not cause hypocalcemia etc.

The peptide of the present invention has been demonstrated to exhibit the desired effects through oral administration to a mammal, and therefore the agent containing the peptide is suitable for oral administration. The peptide of the present invention is highly safe and acts gently, and therefore can be ingested or administered for a long period of time.

Medicaments

The present invention includes a medicament comprising the peptide of the present invention. The peptide of the present invention can be used as an active ingredient of a medicament for prevention and/or treatment of osteogenesis imperfecta, osteoporosis and/or osteoarthritis.

The medicament of the present invention can be produced by appropriately blending the peptide of the present invention as an active ingredient with a pharmaceutically acceptable carrier or additive in accordance with a known production method for pharmaceutical formulations (e.g., the methods described in the Japanese Pharmacopoeia, etc.). In particular, the medicament may be, for example, an oral formulation or a parenteral formulation, including tablets (including sugar-coated tablets, film-coated tablets, sublingual tablets, orally disintegrating tablets, buccal tablets, etc.), pills, powders, granules, capsules (including soft capsules and microcapsules), troches, syrups, liquids, emulsions, suspensions, controlled-release formulations (e.g., fast-release formulations, sustained release formulations, and sustained release microcapsules), aerosols, films (e.g., orally disintegrating films, and oral mucosal adhesive films), injections (e.g., subcutaneous injections, intravenous injections, intramuscular injections, and intraperitoneal injections), intravenous infusions, transdermal formulations, ointments, lotions, patches, suppositories (e.g., rectal suppositories and vaginal suppositories), pellets, transnasal formulations, transpulmonary formulations (inhalants), and eye drops. The amount of the carrier or additive to be added can be determined as appropriate based on the amount range typically used in the pharmaceutical field. The carrier or additive that may be added is not particularly limited and examples thereof include various types of carriers such as water, physiological saline, other aqueous solvents, and aqueous or oily vehicles; and various types of additives such as excipients, binders, pH adjusters, disintegrants, absorption promoters, lubricants, colorants, flavors and fragrances.

Examples of the additives that may be contained in tablets, capsules, etc. include binders such as gelatin, corn starch, tragacanth, and gum arabic; excipients such as crystalline cellulose; swelling agents such as corn starch, gelatin, and alginic acid; lubricants such as magnesium stearate; sweeteners such as sucrose, lactose, and saccharin; and flavors such as peppermint flavor, wintergreen oil, and cherry flavor. When the unit dosage form is a capsule, a liquid carrier such as oils and fats can be further added in addition to the above types of materials. A sterile composition for injection can be prepared in accordance with a usual pharmaceutical practice (for example, by dissolving or suspending the active ingredient in a solvent such as water for injection or a natural vegetable oil). Aqueous liquids for injection that may be used are, for example, physiological saline and an isotonic solution containing glucose and/or other auxiliary substances (for example, D-sorbitol, D-mannitol, sodium chloride, etc.). The aqueous liquids for injection may be used in combination with an appropriate solubilizer, such as alcohols (e.g., ethanol), polyalcohols (e.g., propylene glycol, polyethylene glycol, etc.), and nonionic surfactants (e.g., polysorbate 80™, HCO-50, etc.). Oily liquids that may be used are, for example, sesame oil and soybean oil. The oily liquids may be used in combination with a solubilizer such as benzyl benzoate and benzyl alcohol. Other additives that may be added are, for example, buffering agents (e.g., a phosphate buffer, a sodium acetate buffer, etc.), soothing agents (e.g., benzalkonium chloride, procaine hydrochloride, etc.), stabilizers (e.g., human serum albumin, polyethylene glycol, etc.), preservatives (e.g., benzyl alcohol, phenol, etc.) and antioxidants.

The formulations produced in the above manner are safe and have low toxicity, and thus can be administered to, for example, humans and other mammals (e.g., rats, mice, rabbits, sheep, pigs, cows, cats, dogs, monkeys, etc.). The administration subject may be an infant, a child and an adult.

The amount of the peptide of the present invention contained in the medicament of the present invention may vary with the dosage form, the mode of administration, the carrier to be used, etc., but is usually 0.01 to 100% (w/w), preferably 0.1 to 95% (w/w), based on the total amount of the formulation. The medicament of the present invention containing the peptide of the present invention in such an amount can be produced in accordance with a conventional method.

The dosage varies with the subject to which the medicament is to be administered, the symptoms, the route of administration, etc., but in general, the dosage for oral administration to a human with a body weight of about 60 kg is about 0.01 to 1000 mg per day, preferably about 0.1 to 500 mg per day, more preferably about 0.5 to 100 mg per day, and further preferably 5 to 80 mg per day. The total daily dosage may be administered in a single dose or in divided doses.

The medicament of the present invention exhibits highly additive or synergistic effects when used in combination with another drug. Examples of the drug used in combination with the medicament of the present invention include osteogenesis imperfecta drugs, osteoporosis drugs and osteoarthritis drugs.

Specific examples of the drug used in combination with the medicament of the present invention include, for example, calcium drugs, calcium absorption-promoting drugs, human anti-RANKL monoclonal antibodies, female hormone medicines, selective estrogen receptor modulators (SERMs), calcitonin formulations, bisphosphonates, human parathyroid hormone (PTH), PTHrP analogs, vitamin $K_2$ formulations, anti-Siglec-15 antibodies, anti-TNFα antibodies, IL-1 receptor agonists, anti-IL-6 receptor, anti-sclerostin antibodies, cathepsin K inhibitors, and recombinant human fibroblast growth factor (rhFGF-2). More specifically, examples of the calcium drugs include, but are not limited to, calcium lactate, calcium gluconate (trade name: CALCICOL Injection) and calcium L-aspartate hydrate (trade name: Aspara-CA). Examples of the calcium absorption-promoting drugs include, but are not limited to, alfacalcidol (trade name: Alfarol, Onealfa), calcitriol (trade name: Rocaltrol), falecalcitriol (trade name: Fulstan) and eldecalcitol (trade name: Edirol). Examples of the human anti-RANKL monoclonal antibodies include, but are not limited to, denosumab (trade name: Prolia). Examples of the female hormone medicines include, but are not limited to, estriol (trade name: Holin, Estriel), conjugated estrogens (Premarin) and estradiol (trade name: Estrana). Examples of the selective estrogen receptor modulators (SERMs) include, but are not limited to, raloxifene hydrochloride (trade name: Evista) and bazedoxifene acetate (trade name: Viviant). Examples of the calcitonin formulations include, but are not limited to, elcatonin (trade name: Elcitonin) and salmon calcitonin (trade name: Calcitoran). Examples of the bisphosphonates include, but are not limited to, etidronate disodium (trade name: Didronel), alendronate sodium (trade name: Bonalon, Fosamac), risedronate sodium (trade name: Benet, Actonel), minodronic acid (trade name: Recalbon, Bonoteo), ibandronate sodium hydrate (trade name: Bonviva Injection) and ibandronate sodium (trade name: Bonviva Tablet). Examples of the human parathyroid hormone (PTH) include, but are not limited to, teriparatide (trade name: Teribone, Forteo). Examples of the PTHrP analogs include, but are not limited to, abaloparatide. Examples of the vitamin $K_2$ formulations include, but are not limited to, menatetrenone (trade name: Kaytwo, Glakay). Examples of the anti-sclerostin antibodies include, but are not limited to, romosozumab (trade name). Examples of the cathepsin K inhibitors include, but are not limited to, odanacatib (trade name).

Other examples of the drug used in combination with the medicament of the present invention include bisphosphonates. Examples of the bisphosphonates include, but are not limited to, pamidronate disodium hydrate (trade name: Aredia).

Further examples of the drug used in combination with the medicament of the present invention include nonsteroidal antiinflammatory drugs (NSAIDs), tropomyosin-related kinase (Trk) A inhibitors, adenosine A3 receptor agonists, glucocorticoid receptor agonists, hyaluronic acid, fibroblast growth factor-18 inhibitors, anti-GM-CSF (granulocyte-macrophage colony-stimulating factor) antibodies, and anti-NGF (nerve growth factor) antibodies. Examples of the nonsteroidal antiinflammatory drugs (NSAIDs) include, but are not limited to, (S)-flurbiprofen. Examples of the adenosine A3 receptor agonists include, but are not limited to, piclidenoson. Examples of the glucocorticoid receptor agonists include, but are not limited to, triamcinolone acetonide. Examples of the hyaluronic acid include, but are not limited to, purified hyaluronate sodium (trade name: Artz, Suvenyl). Examples of the fibroblast growth factor-18 inhibitors include, but are not limited to, sprifermin. Examples of the anti-NGF (nerve growth factor) antibodies include, but are not limited to, fulranumab.

Further examples of the drug used in combination with the medicament of the present invention include a compound that has an inhibitory effect on osteoclasts or a bisphosphonate. Even when used in combination with any of these drugs, the agent or medicament of the present invention is suitable for use in the prevention and/or treatment of osteogenesis imperfecta, osteoporosis and/or osteoarthritis, in particular, for use in the promotion of osteogenesis, the promotion of the healing of bone fractures, or other applications in relation to the symptoms of the disorders, because the agent or medicament of the present invention does not affect osteoclasts.

In an embodiment of a combination comprising (A) the agent or medicament of the present invention and (B) another medicament for preventing and/or treating osteogenesis imperfecta, osteoporosis and/or osteoarthritis, (A) the agent or medicament may be administered together with (B) another medicament, or (A) the agent or medicament may be mixed with (B) another medicament before use.

In the present invention, when (A) the agent or medicament is administered together with (B) another medicament, the timing of administration of (A) the agent or medicament and (B) another medicament is not particularly limited, and pre-administration, simultaneous administration or post-administration of (A) the agent or medicament, or any combination thereof may be performed. The term "pre-administration" of (A) the agent or medicament as used herein means that (A) the agent or medicament is administered to a subject over a certain period of time before the administration of (B) another medicament. The term "simultaneous administration" of (A) the agent or medicament as used herein means that (A) the agent or medicament is administered to a subject throughout the period of time from the start to the end of the administration of (B) another medicament, or means that (A) the agent or medicament is administered to a subject over a certain period of time within the period of time from the start to the end of the administration of (B) another medicament. The term "post-administration" of (A) the agent or medicament as used herein means that (A) the agent or medicament is administered to a subject over a certain period of time after the end of administration of (B) another medicament. The duration of administration of (A) the agent or medicament and (B) another medicament is not particularly limited, and may be, for example, about 1 to 30 minutes or about 1 to 12 hours.

In an embodiment of the medicament of the present invention, wherein (A) the agent or medicament is mixed with (B) another medicament before use, the mixing ratio of (A):(B) is not particularly limited, and may be, for example, 1:0.001 to 1000, 1:0.01 to 100, 1:0.1 to 10 or 1:0.5 to 2.

The present invention also includes the agent or medicament of the present invention for promoting osteogenesis. The promotion of osteogenesis herein refers to, for example, the promotion of osteoblast proliferation, the promotion of chondrocyte proliferation, the promotion of bone growth, an increase in the calcification rate, etc., or any combination of two or more thereof. Specific examples of the bone herein include, but are not limited to, primary cancellous bone, secondary cancellous bone, bone marrow, epiphysis, metaphysis, diaphysis, preliminary calcification layer, growth plate, hypertrophic cartilage layer, growth plate cartilage, long bones, femur, patella, fibula, tibia and cortical bones.

The present invention further includes the following.

(a) A method for preventing and/or treating osteogenesis imperfecta, osteoporosis and/or osteoarthritis, the method comprising administering, to a mammal, an effective amount of the agent or peptide of the present invention (the peptides consisting of the amino acid sequences of SEQ ID NOs: 1 and 2, including a salt, a ester, a derivative and a modified form thereof as described above; the same applies hereinafter).

(b) The agent or peptide of the present invention for use in the prevention and/or treatment of osteogenesis imperfecta, osteoporosis and/or osteoarthritis.

(c) Use of the agent or peptide of the present invention for the prevention and/or treatment of osteogenesis imperfecta, osteoporosis and/or osteoarthritis.

(d) Use of the agent or peptide of the present invention in the production of a medicament for the prevention and/or treatment of osteogenesis imperfecta, osteoporosis and/or osteoarthritis.

(e) A method for preventing a bone fracture and/or promoting the healing of a bone fracture, the method comprising administering an effective amount of the agent or peptide of the present invention to a mammal.

(f) The agent or peptide of the present invention for use in the prevention of a bone fracture and/or the promotion of the healing a bone fracture.

(g) Use of the agent or peptide of the present invention for the prevention of a bone fracture and/or the promotion of the healing of a bone fracture.

(h) Use of the agent or peptide of the present invention for the production of a medicament for the prevention of a bone fracture and/or the promotion of the healing of a bone fracture.

(i) A food or drink product, a food additive, an animal feed, a feed additive and a cosmetic product, each comprising the agent or peptide of the present invention.

Food and Drink Products

The food and drink products of the present invention are suitable as food and drink products for the prevention of osteogenesis imperfecta, osteoporosis and/or osteoarthritis, as food and drink products for the prevention of a bone fracture and/or the promotion of the healing of a bone fracture, or as other types of food and drink products.

The food and drink products of the present invention include health foods, functional foods, foods for specified health use, foods for sick people and dietary supplements, each containing the agent or peptide of the present invention. The form of the food and drink products is not particularly limited, and may be, for example, a tablet, granules, a powder, an energy drink, etc. Examples of the food and drink products of the present invention include drinks such as tea drinks, refreshing drinks, carbonated drinks, nutritional drinks, fruit juice, and lactic drinks; noodles such as buckwheat noodles, wheat noodles, Chinese noodles, and instant noodles; sweets and bakery products such as drops, candies, gum, chocolate, snacks, biscuits, jelly, jam, cream, pastry, and bread; fishery and livestock products such as fish sausages, ham, and sausages; dairy products such as processed milk and fermented milk; fats, oils, and processed foods thereof, such as vegetable oils, oils for deep frying, margarine, mayonnaise, shortening, whipped cream, and dressing; seasonings such as sauce and dipping sauce; retort pouch foods such as curry, stew, rice-bowl cuisine, porridge, and rice soup; and frozen desserts such as ice cream, sherbet, and shaved ice.

Food Additives, Animal Feeds and Feed Additives

The food additive of the present invention is suitable as a food additive for the prevention of osteogenesis imperfecta, osteoporosis and/or osteoarthritis, as a food additive for the prevention of a bone fracture and/or the promotion of the healing of a bone fracture, or as other types of food additives. The form of the food additive of the present invention is not particularly limited, and may be, for example, a liquid, a paste, a powder, flakes, granules, etc. The food additive of the present invention can be produced in accordance with a conventional production method for food additives.

The present invention also provides a feed or a feed additive containing the peptide of the present invention.

Cosmetic Products

The cosmetic product of the present invention is suitable as a cosmetic product for the prevention of osteogenesis imperfecta, osteoporosis and/or osteoarthritis, as a cosmetic product for the prevention of a bone fracture and/or the promotion of the healing of a bone fracture, or as other types of cosmetic products. The cosmetic product includes the so-called medicated cosmetics (quasi drugs). Examples of the cosmetic product include washing lotions, shampoos, rinses, hair tonics, hair lotions, aftershave lotions, body lotions, makeup lotions, cleansing creams, massage creams, emollient creams, aerosol products, deodorizers, fragrances, deodorants, and bath fragrances. Depending on the purpose, the cosmetic product of the present invention may contain an ingredient generally used in cosmetic products in addition to the peptide of the present invention, and such an ingredient includes, for example, surfactants, moisturizers, animal- and plant-derived fats and oils, silicones, higher alcohols, lower alcohols, animal- and plant-derived extracts, ultraviolet absorbers, anti-inflammatories, sequestering agents, vitamins, antioxidants, thickeners, preservatives, bactericides, pH adjusters, colorants, and various fragrances.

EXAMPLES

The present invention will be described in more detail below with reference to Examples, but the present invention is not limited thereto.

Production Example: Production of Synthetic Peptides Nos. 1 and 2

Figure 2:
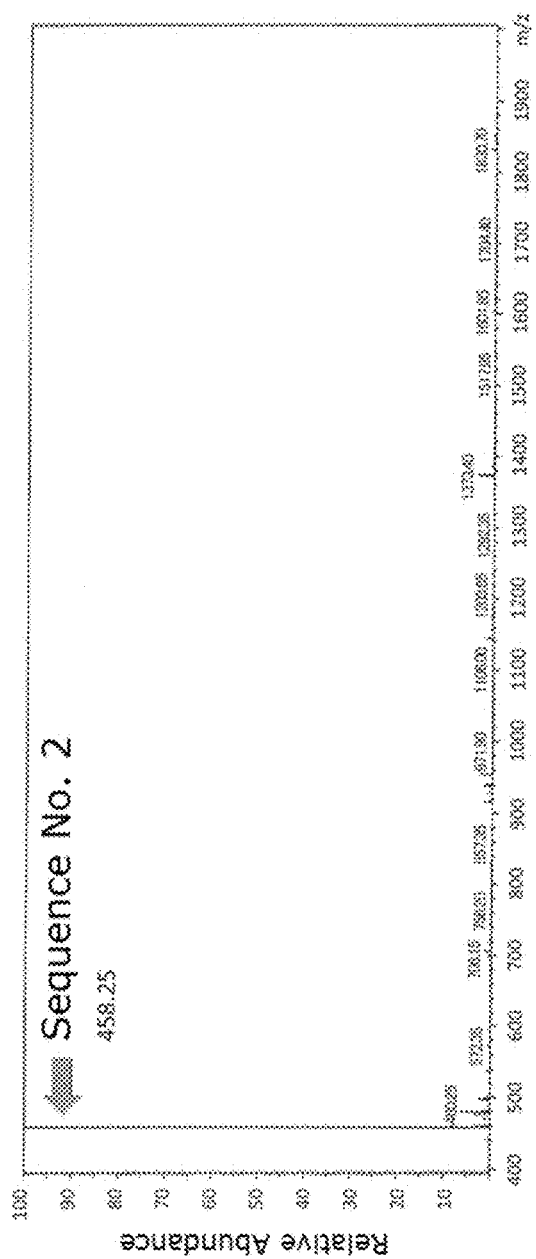
FIG. 2 is a graph showing the analysis results of a synthetic peptide (No. 2).

Synthetic peptides Nos. 1 and 2 were chemically synthesized with a Syro II automatic peptide synthesizer (Biotage Japan Ltd.). The single peaks in the graphs of FIGS. 1 and 2 correspond to the synthetic peptides Nos. 1 and 2 of interest, respectively.

Example 1: Study of Proliferation-Promoting Activity of Synthetic Peptides on Osteoblastic Precursor Cells The mouse osteoblast-like cell line MC3T3-E1 Subclone-4 (ATCC No. CRL-2593) was cultured in α-MEM medium supplemented with 10% FBS at 37° C. in 5% $CO_2$-95% air to subconfluence. The cells were collected by trypsinization. The collected cells were suspended at $5 \times 10^4$ cells/mL in fresh α-MEM medium with the same supplement. One hundred microliters of the cell suspension was seeded in each well of a 96-well plate, and precultured at 37° C. in 5% $CO_2$-95% air. On the next day, the medium was replaced with α-MEM medium containing the sample dissolved therein with a supplement of 0.1% FBS. The cells were further cultured for 24 hours. The proliferative activity of the osteoblastic precursor cells was assessed by measuring the amount of BrdU uptake. The proliferation-promoting activity of the sample on the osteoblastic precursor cells was expressed as a value relative to the proliferation level of the cells in the absence of the sample, which was taken as 100.

Figure 3:
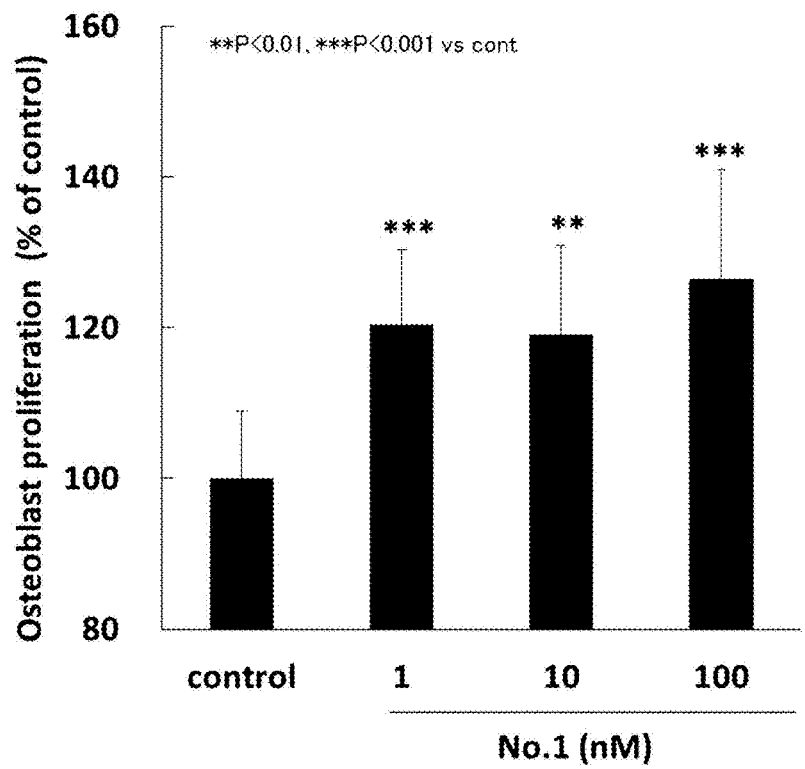
FIG. 3 is a graph showing the measurement results of the proliferation-promoting activity of a synthetic peptide (No. 1) on osteoblastic precursor cells.
Figure 4:
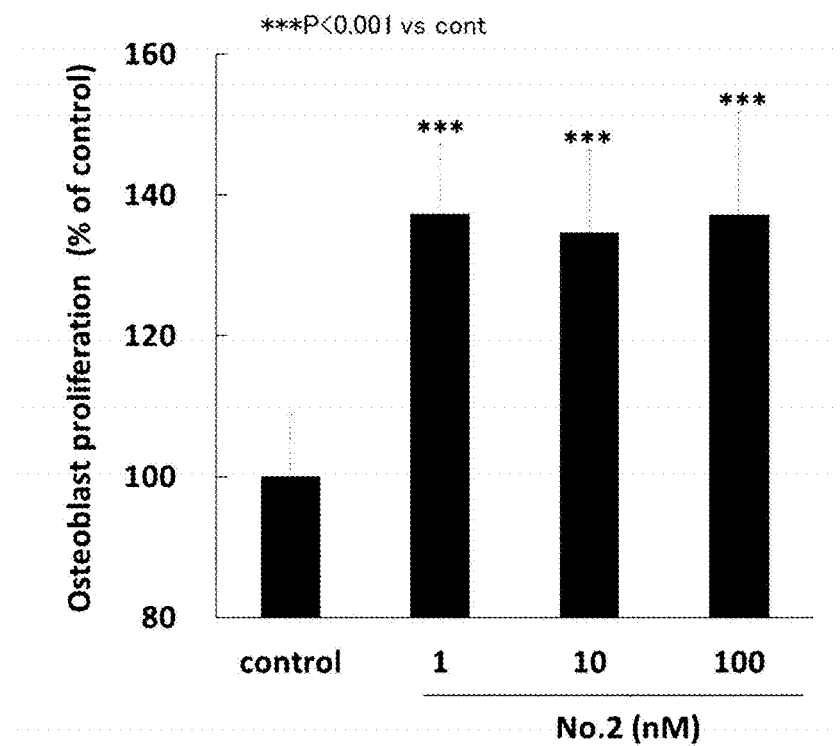
FIG. 4 is a graph showing the measurement results of the proliferation-promoting activity of a synthetic peptide (No. 2) on osteoblastic precursor cells.

The results are shown in FIGS. 3 and 4. The synthetic peptides Nos. 1 and 2 promoted the proliferation of the osteoblastic precursor cells. The synthetic peptide No. 2 has a higher activity than the synthetic peptide No. 1, and sufficiently exhibited its effect at a low concentration.

Example 2: Study of Proliferation-Promoting Activity of Synthetic Peptides on Chondrogenic Cells The mouse chondrogenic cell line ATDC5 (RCB0565) was cultured in DMEM/F-12 medium supplemented with 5% FBS, $3 \times 10^{-8}$ M sodium selenite and 5 μg/mL human transferrin at 37° C. in 5% $CO_2$-95% air to subconfluence. The cells were collected by trypsinization. The collected cells were suspended at $5 \times 10^4$ cells/mL in fresh DMEM/F-12 medium with the same supplements. One hundred microliters of the cell suspension was seeded in each well of a 96-well plate, and precultured at 37° C. in 5% $CO_2$-95% air. On the next day, the medium was replaced with DMEM/F-12 medium containing the sample dissolved therein with a supplement of $3 \times 10^{-8}$ M sodium selenite and 5 μg/mL human transferrin. The cells were further cultured for 24 hours. The proliferative activity of the chondrogenic cells was assessed by measuring the amount of BrdU uptake. The proliferation-promoting activity of the sample on the chondrogenic cells was expressed as a value relative to the proliferation level of the cells in the absence of the sample, which was taken as 100.

Figure 5:
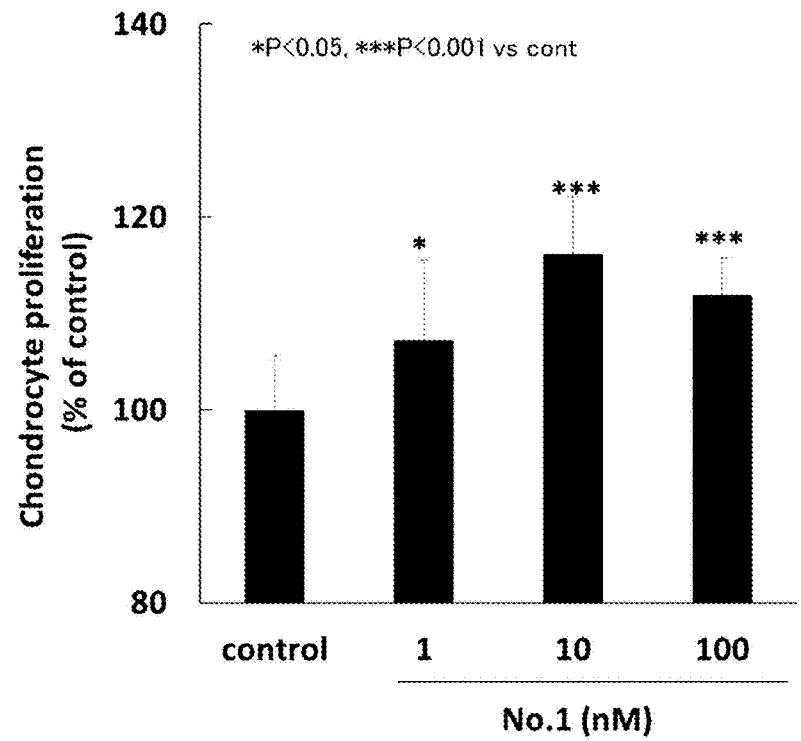
FIG. 5 is a graph showing the measurement results of the proliferation-promoting activity of a synthetic peptide (No. 1) on chondrogenic cells.
Figure 6:
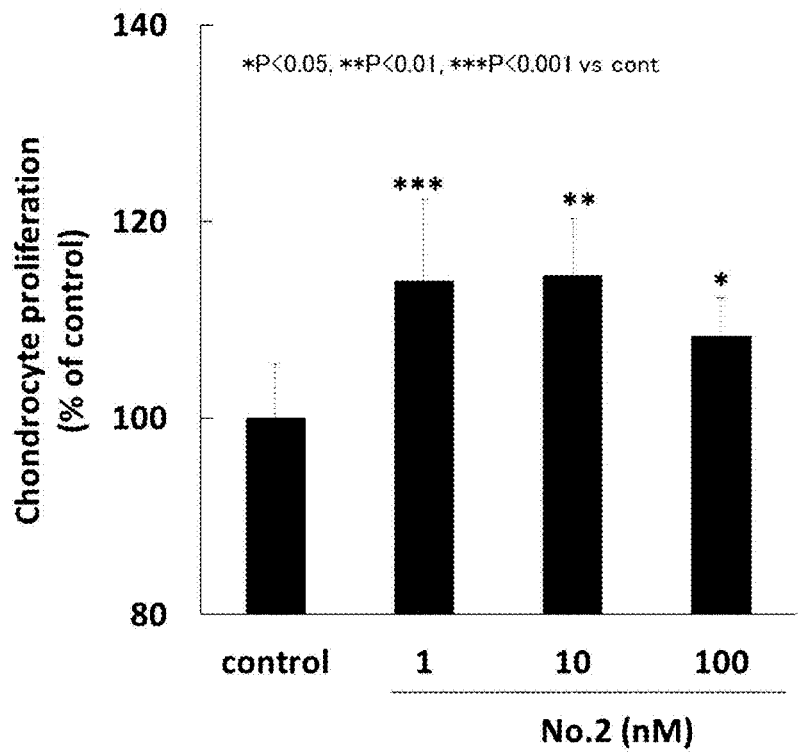
FIG. 6 is a graph showing the measurement results of the proliferation-promoting activity of a synthetic peptide (No. 2) on chondrogenic cells.

The results are shown in FIGS. 5 and 6. The synthetic peptides Nos. 1 and 2 promoted the proliferation of the chondrogenic cells.

Figure 7:
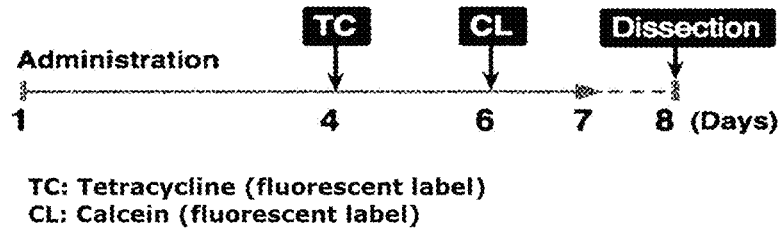
FIG. 7 shows the experimental protocol of Example 3.

Example 3: Study of Bone Growth-Promoting Effect of Synthetic Peptides on Rats in the Growth Phase The synthetic peptide No. 1 or water for injection (control) was administered to male Crlj:WI rats at the age of four weeks by oral gavage using a gastric tube once a day for seven days (n=10 in each group). The dosage of the synthetic peptide was 1, 10 or 100 mg/kg/day. As a positive control, human growth hormone (hGH) (Norditropin, Japan Standard Commodity Classification Number: 872412) was subcutaneously administered at 500 μg/kg/day once a day for seven days. As fluorescent labels for the bone formation site, tetracycline (20 mg/kg) was subcutaneously administered on day 4 after the administration of the peptide or controls, and then calcein (10 mg/kg) was subcutaneously administered on day 6 after the administration of the peptide or controls. After the administration of the sample on day 7, the rats were kept under fasting conditions. Twenty-four hours later, the rats were euthanized by bloodletting under anesthesia, and the tibia was harvested (see FIG. 7). Undecalcified specimens of the proximal tibia were prepared and photographed under a fluorescent microscope (BX-53, Olympus Corporation), and the bone morphology was measured using a morphometry system (Histometry RT digitizer, System Supply Co., Ltd.). The longitudinal growth rate (Lo.G.R.) of the growth plate per day was determined by measuring the distance between the tetracycline and calcein labels and dividing the distance by the time interval between the administrations of the two fluorescent labels (two days).

Figure 8:
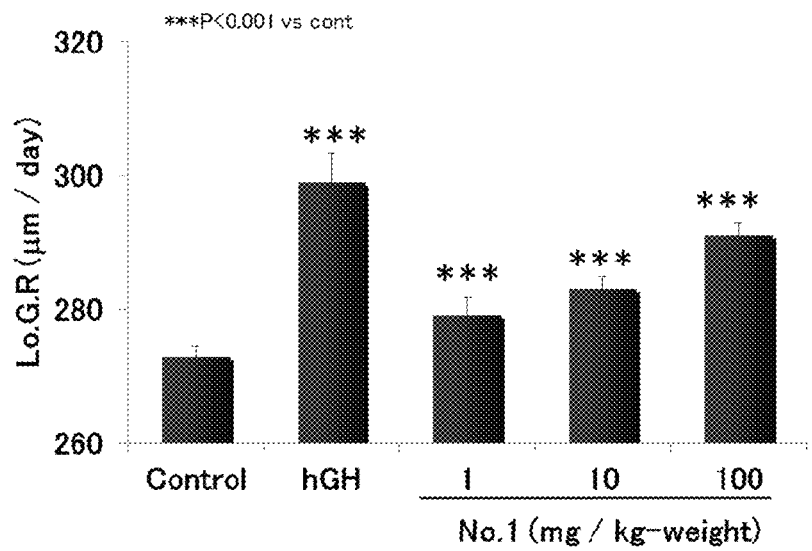
FIG. 8 is a graph showing the growth rate of the growth plate per day (in the longitudinal direction) in synthetic peptide (No. 1) administration groups.
Figure 9:
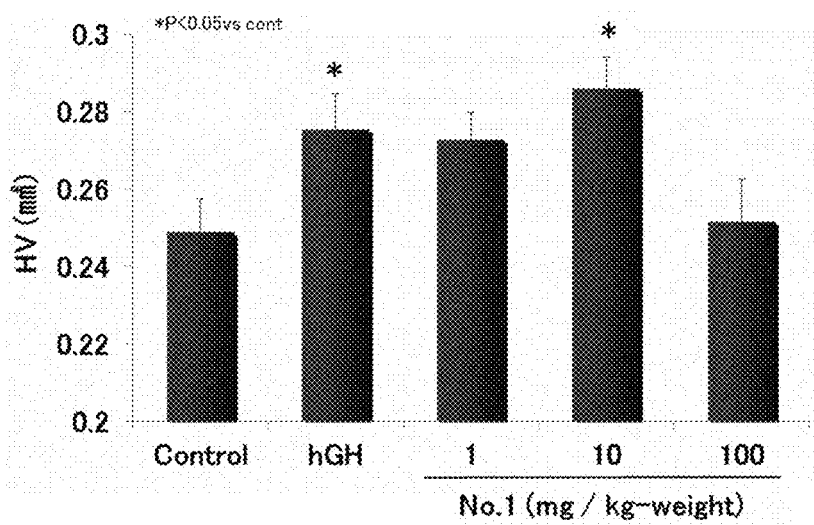
FIG. 9 is a graph showing the area of the hypertrophic cartilage layer in the growth plate of rats in synthetic peptide (No. 1) administration groups.

The hGH and synthetic peptide No. 1 administration groups showed significant promotion of bone growth as compared with the control group, and the effect of the synthetic peptide No. 1 increased in a dose-dependent manner (FIG. 8). The area of the hypertrophic cartilage layer was also measured and was found to be significantly larger in the hGH and synthetic peptide No. 1 (10 mg/kg/day) administration groups than in the control group (FIG. 9).

Figure 10:
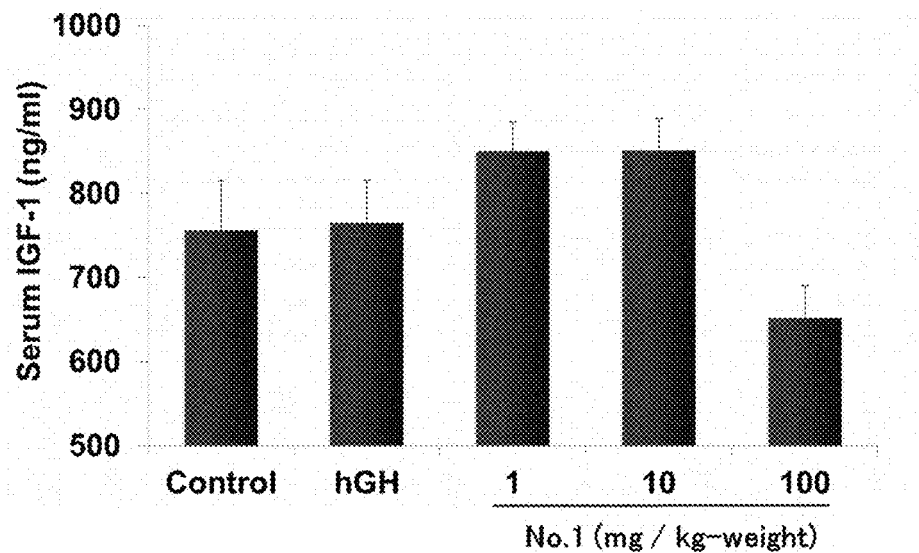
FIG. 10 is a graph showing the concentration of insulin-like growth factor (IGF-1) in the serum of rats in synthetic peptide (No. 1) administration groups.

From the same rats as above, which received sample administration for seven days and were then kept under fasting conditions for 24 hours, the blood was collected and the serum was separated. The concentration of insulin-like growth factor (IGF-1) in the serum was measured by ELISA (Mouse/Rat IGF-I Quantikine ELISA Kit (MG100), R&D Systems, Inc.). The serum IGF-1 concentrations in the synthetic peptide No. 1 administration groups (1 and 10 mg/kg/day) tended to be higher than that in the control group (FIG. 10). The results indicated that the increase in the concentration of IGF-1, which plays a role in osteogenesis and muscle growth in the growth phase, contributes to the bone growth-promoting effect.

The overall results showed that oral administration of the peptide of the present invention promotes longitudinal bone growth in the growth phase.

Figure 11:
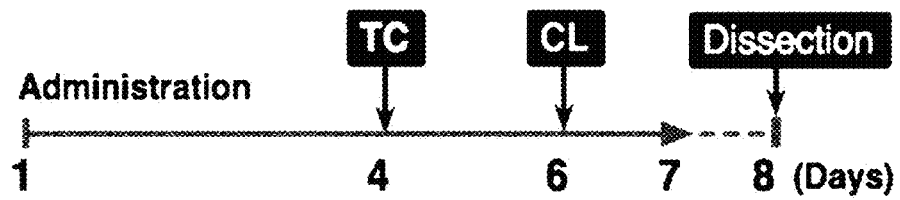
FIG. 11 shows the experimental protocol of Example 4.

Example 4: Study of Osteogenesis-Promoting Effect of Synthetic Peptides on Primary Cancellous Bone The synthetic peptide No. 1 or water for injection (control) was administered to male Crlj:WI rats at the age of four weeks by oral gavage using a gastric tube once a day for seven days (n=3 in each group). The dosage of the synthetic peptide was 100 mg/kg/day. As a positive control, human growth hormone (hGH) (Norditropin, Japan Standard Commodity Classification Number: 872412) was subcutaneously administered at 500 μg/kg/day once a day for seven days. As fluorescent labels for the bone formation site, tetracycline (20 mg/kg) was subcutaneously administered on day 4 after the administration of the peptide or controls, and then calcein (10 mg/kg) was subcutaneously administered on day 6 after the administration of the peptide or controls. After the administration of the sample on day 7, the rats were kept under fasting conditions. Twenty-four hours later, the rats were euthanized by bloodletting under anesthesia, and the tibia was harvested (see FIG. 11). Undecalcified specimens of the proximal tibia were prepared and photographed under a fluorescent microscope (BX-53, Olympus Corporation), and the bone morphology was measured using a morphometry system (Histometry RT digitizer, System Supply Co., Ltd.).

Figure 12:
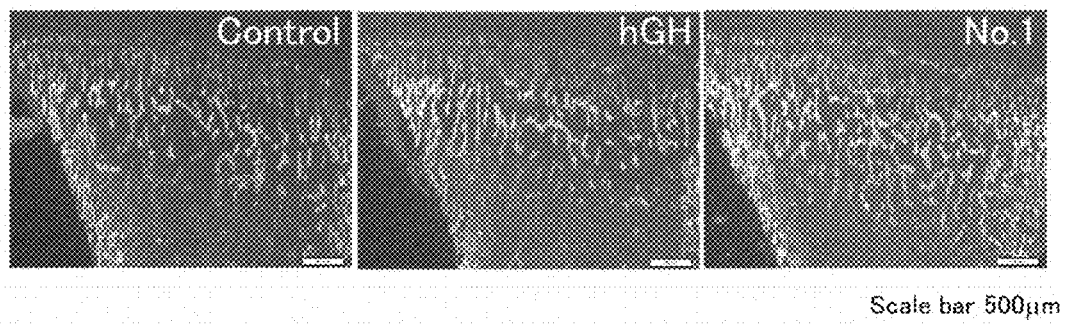
FIG. 12 shows the fluorescent microscope images of the formation of the primary cancellous bone of rats in a synthetic peptide (No. 1) administration group.

The fluorescent labels incorporated into the primary cancellous bone were more highly detected in the synthetic peptide No. 1 administration group than in the control group and the hGH administration group, indicating that the synthetic peptide induces rapid formation of the cancellous bone in the growth phase (FIG. 12, white region).

The above results revealed that oral administration of the peptide of the present invention promotes the formation of the primary cancellous bone.

Figure 13:
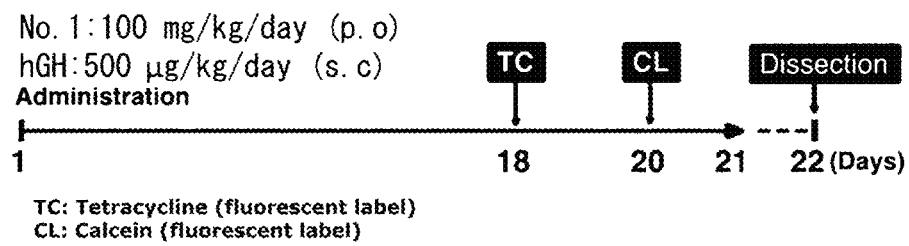
FIG. 13 shows the experimental protocol of Example 5.

Example 5: Study of Osteogenesis-Promoting Effect of Synthetic Peptides on Growth Plate and Secondary Cancellous Bone The synthetic peptide No. 1 or water for injection (control) was administered to male Crlj:WI rats at the age of four weeks by oral gavage using a gastric tube once a day for 21 days. The dosage of the synthetic peptide was 100 mg/kg/day. As a positive control, human growth hormone (hGH) was subcutaneously administered at 500 µg/kg/day once a day for 21 days. As fluorescent labels for the bone formation site, tetracycline (20 mg/kg) was subcutaneously administered on day 18 after the administration of the peptide or controls, and then calcein (10 mg/kg) was subcutaneously administered on day 20 after the administration of the peptide or controls. After the administration of the sample on day 21, the rats were kept under fasting conditions. Twenty-four hours later, the rats were euthanized by bloodletting under anesthesia, and the tibia was harvested (see FIG. 13). Undecalcified specimens of the proximal tibia were prepared and photographed under a fluorescent microscope (BX-53, Olympus Corporation), and the bone morphology was measured using a morphometry system (Histometry RT digitizer, System Supply Co., Ltd.) and an analysis software (CSS-840 cancellous bone morphometry version, System Supply Co., Ltd.). The longitudinal growth rate (Lo.G.R.) of the epiphyseal plate per day was determined by measuring the distance between the tetracycline and calcein labels and dividing the distance by the time interval between the administrations of the two fluorescent labels (two days).

Figure 14:
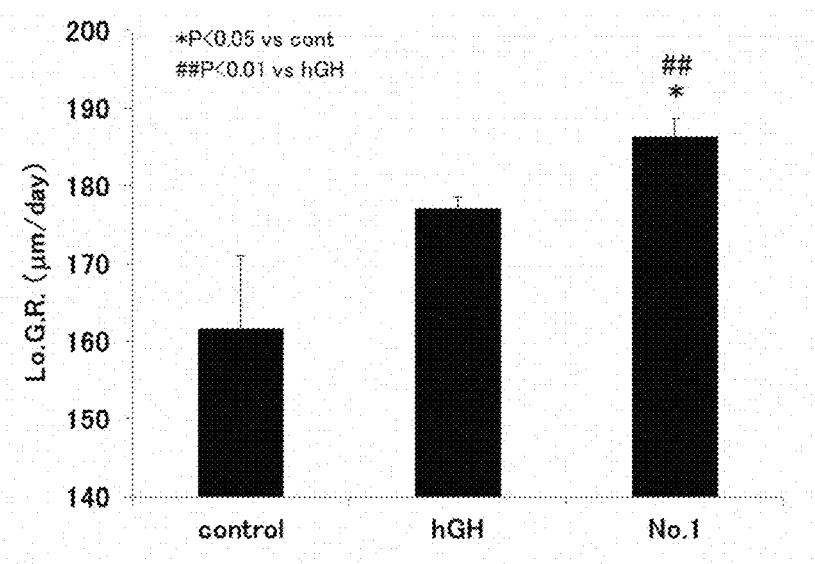
FIG. 14 is a graph showing the growth rate of the growth plate per day (in the longitudinal direction) in a synthetic peptide (No. 1) administration group.

The hGH and synthetic peptide No. 1 administration groups showed significant promotion of bone growth as compared with the control group, and the bone growth-promoting effect observed in the synthetic peptide No. 1 administration group was significantly higher than that in the hGH administration group (FIG. 14). The results indicated that long-term oral administration of the peptide of the present invention also promotes longitudinal bone growth in the growth phase.

Figure 15:
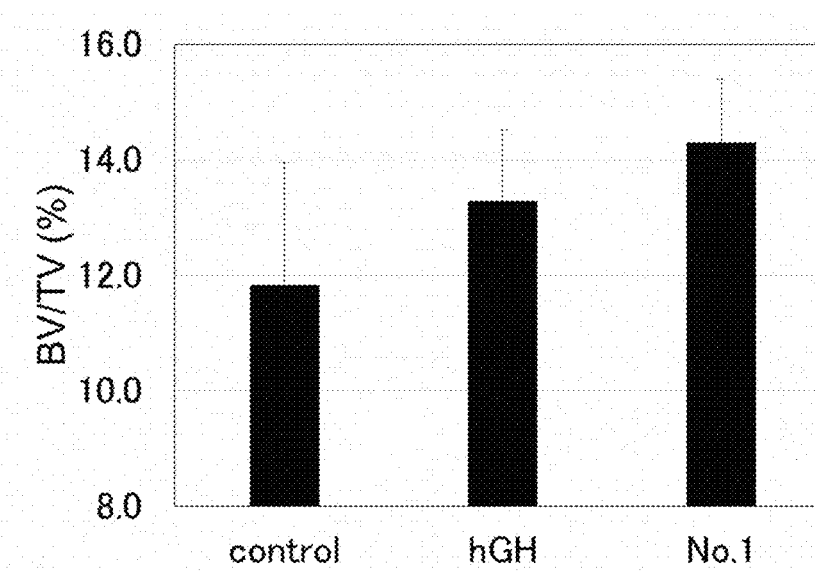
FIG. 15 is a graph showing the volume of the secondary cancellous bone of rats in a synthetic peptide (No. 1) administration group.
Figure 16:
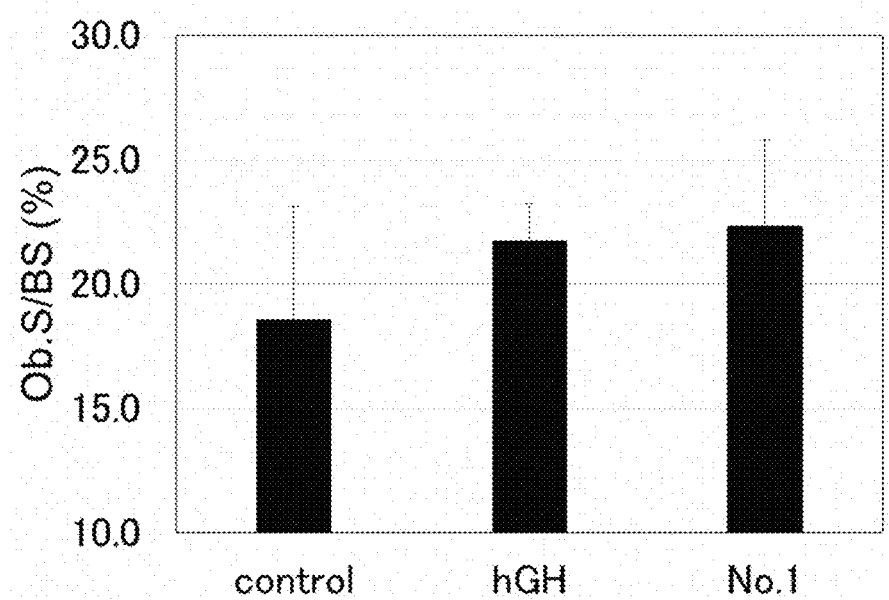
FIG. 16 is a graph showing the percentage of the bone surface occupied by osteoblasts relative to the total bone surface in a synthetic peptide (No. 1) administration group.
Figure 17:
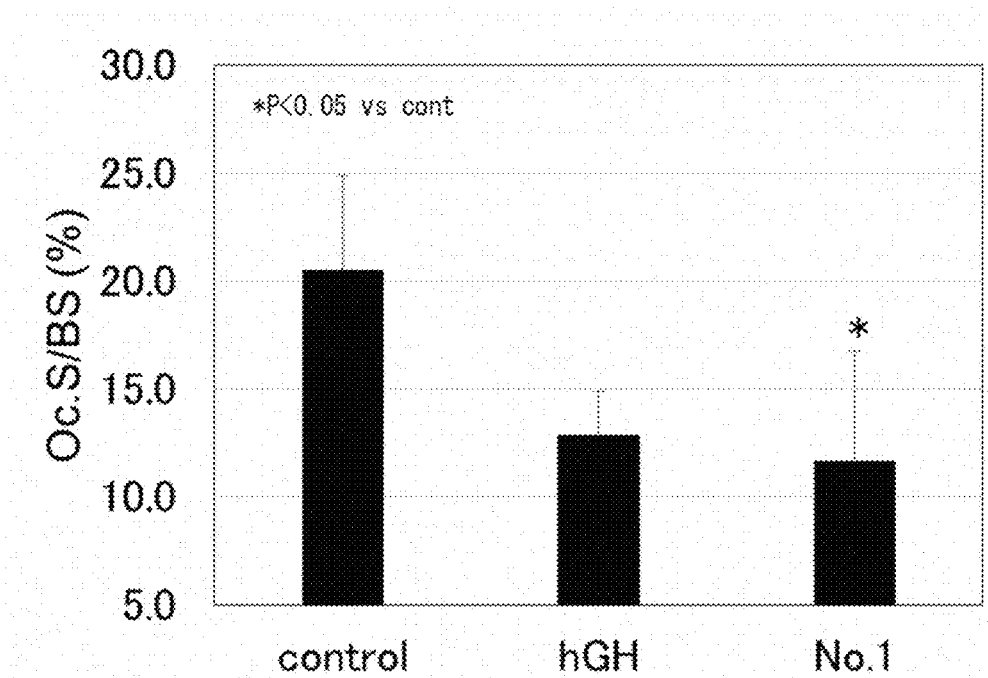
FIG. 17 is a graph showing the percentage of the bone surface occupied by osteoclasts relative to the total bone surface in a synthetic peptide (No. 1) administration group.

The analysis of the secondary cancellous bone volume (bone volume/tissue volume (BV/TV)) by the above analysis system showed that the synthetic peptide No. 1 administration group had a higher secondary cancellous bone volume than the control group and the hGH administration group (FIG. 15). The synthetic peptide No. 1 administration group also showed a higher percentage of the bone surface occupied by osteoblasts relative to the total bone surface (osteoblast surface/bone surface (Ob.S/BS))(FIG. 16) and a lower percentage of the bone surface occupied by osteoclasts relative to the total bone surface (osteoclast surface/Bone surface (Oc.S/BS))(FIG. 17).

The overall results showed that oral administration of the peptide of the present invention induces bone metabolism in which bone formation is predominant, thereby increasing the bone volume.

Example 6: Study of Accelerating Effect of Synthetic Peptides on Calcification Rate in Secondary Cancellous Bone The synthetic peptide No. 1 or water for injection (control) was administered to male Crlj:WI rats at the age of four weeks by oral gavage using a gastric tube once a day for seven days (n=10 in each group). The dosage of the synthetic peptide was 1, 10 or 100 mg/kg/day. As a positive control, human growth hormone (hGH) (Norditropin, Japan Standard Commodity Classification Number: 872412) was subcutaneously administered at 500 µg/kg/day once a day for seven days. As fluorescent labels for the bone formation site, tetracycline (20 mg/kg) was subcutaneously administered on day 4 after the administration of the peptide or controls, and then calcein (10 mg/kg) was subcutaneously administered on day 6 after the administration of the peptide or controls. After the administration of the sample on day 7, the rats were kept under fasting conditions. Twenty-four hours later, the rats were euthanized by bloodletting under anesthesia, and the tibia was harvested (see FIG. 7). Undecalcified specimens of the proximal tibia were prepared and photographed under a fluorescent microscope (BX-53, Olympus Corporation), and the bone morphology was measured using a morphometry system (Histometry RT digitizer, System Supply Co., Ltd.). The daily calcification rate (mineral apposition rate) was determined by measuring the distance between the tetracycline and calcein labels in the secondary cancellous bones and dividing the distance by the time interval between the administrations of the two fluorescent labels (two days).

Figure 18:
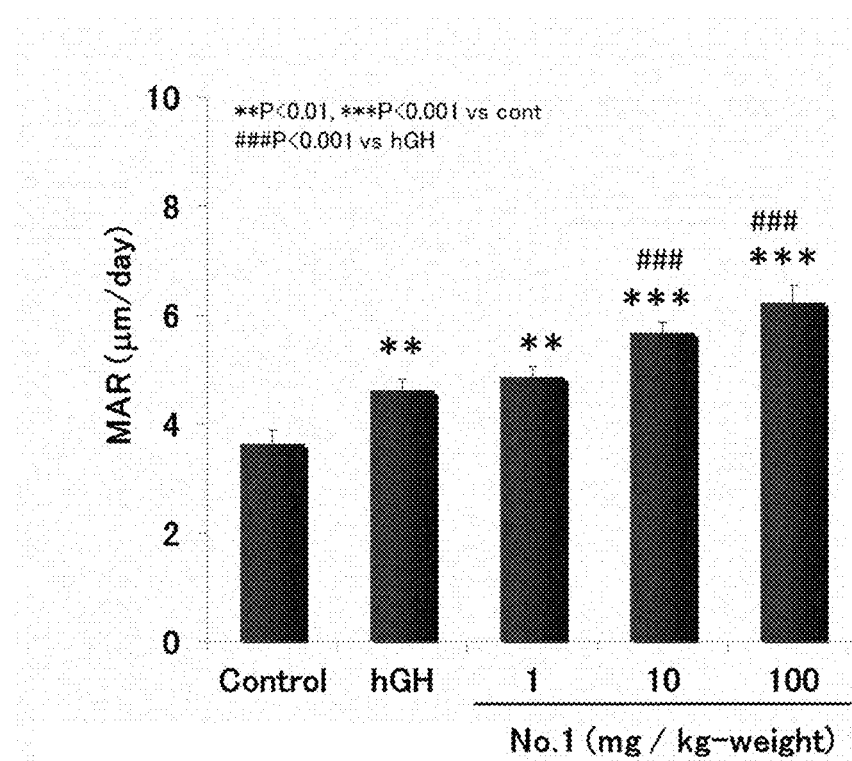
FIG. 18 is a graph showing the calculated daily calcification rate in the secondary cancellous bone of rats in synthetic peptide (No. 1) administration groups.
Figure 19:
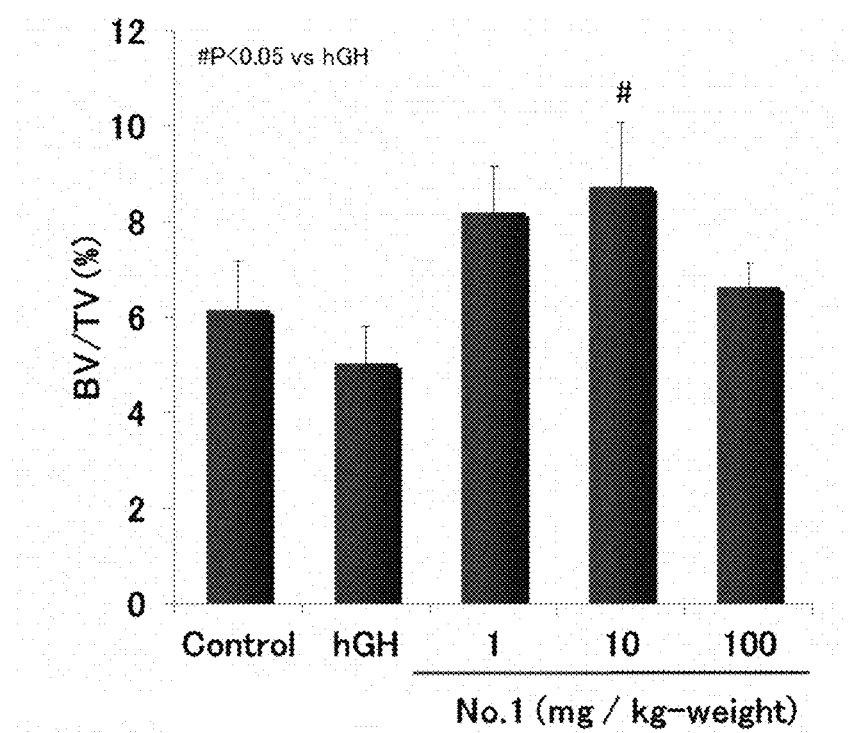
FIG. 19 is a graph showing the volume of the secondary cancellous bone of rats in synthetic peptide (No. 1) administration groups.
Figure 20:
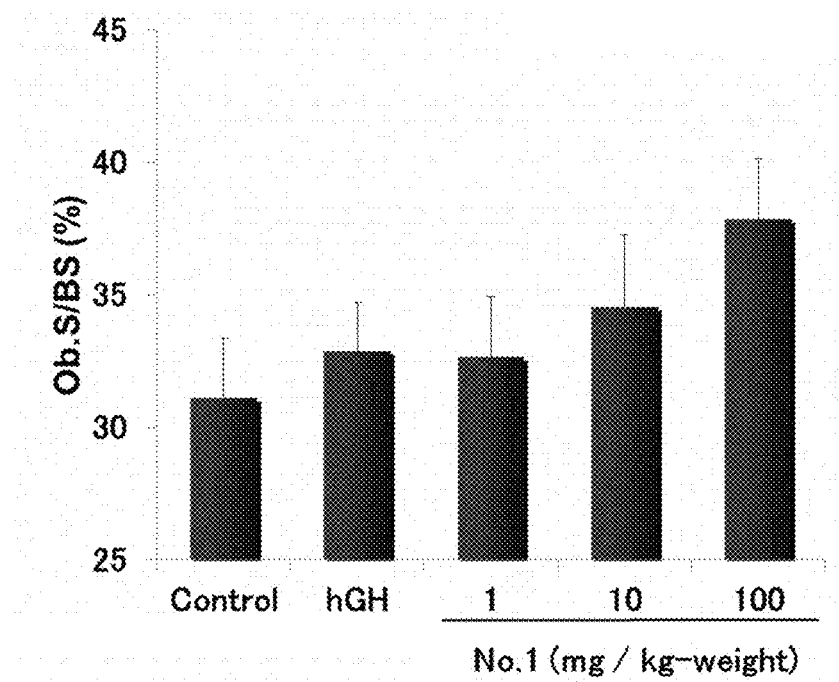
FIG. 20 is a graph showing the percentage of the bone surface occupied by osteoblasts relative to the total bone surface in synthetic peptide (No. 1) administration groups.
Figure 21:
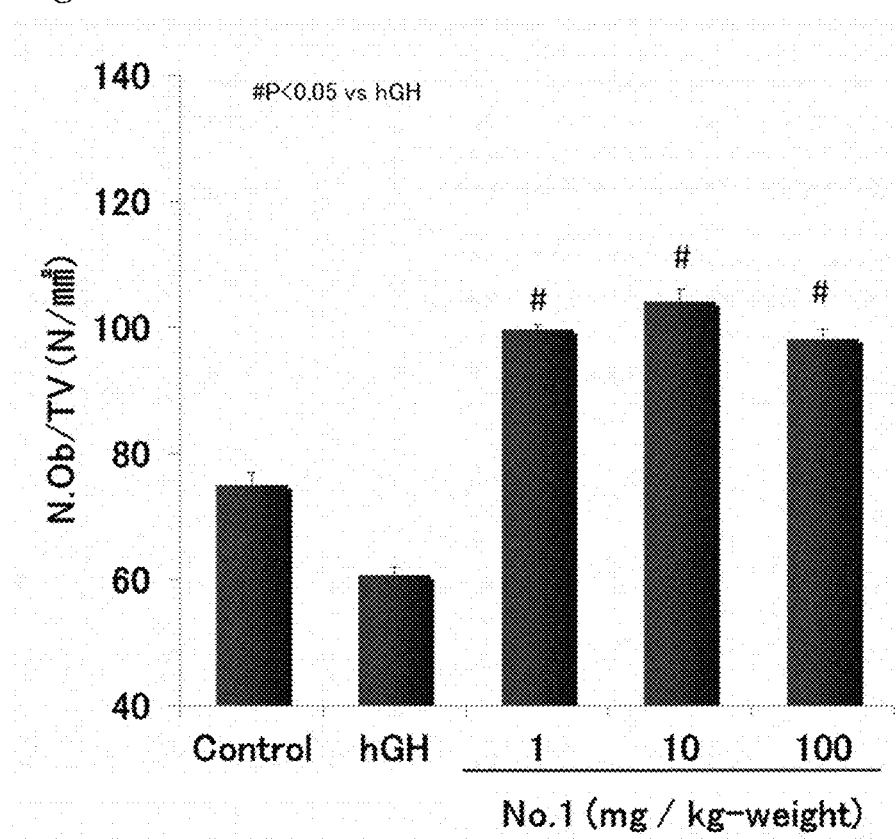
FIG. 21 is a graph showing the number of osteoblasts per unit bone surface of rats in synthetic peptide (No. 1) administration groups.
Figure 22:
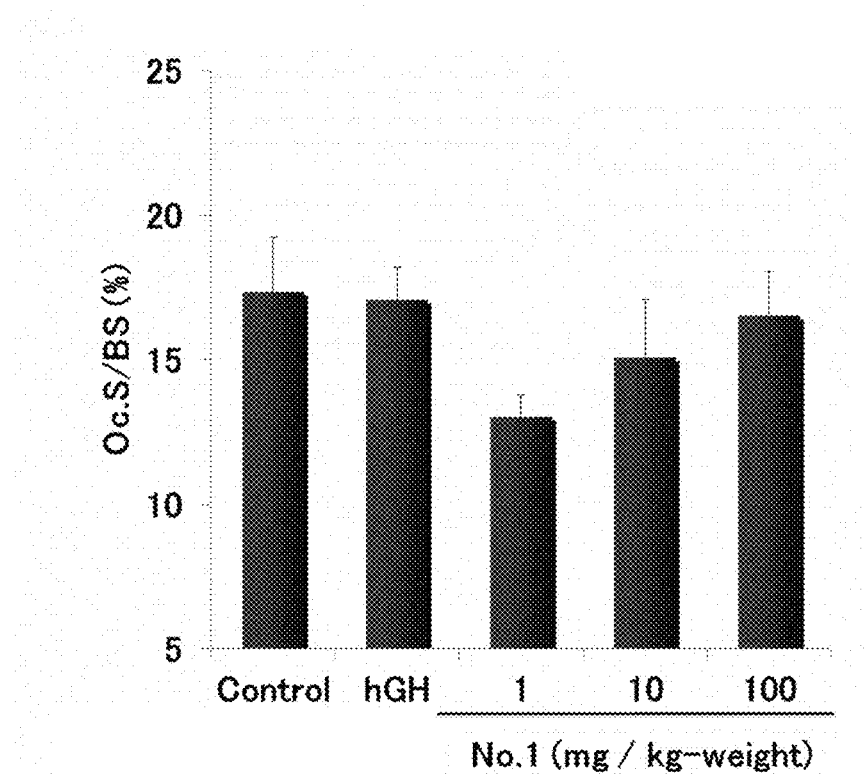
FIG. 22 is a graph showing the percentage of the bone surface occupied by osteoclasts relative to the total bone surface in synthetic peptide (No. 1) administration groups.
Figure 23:
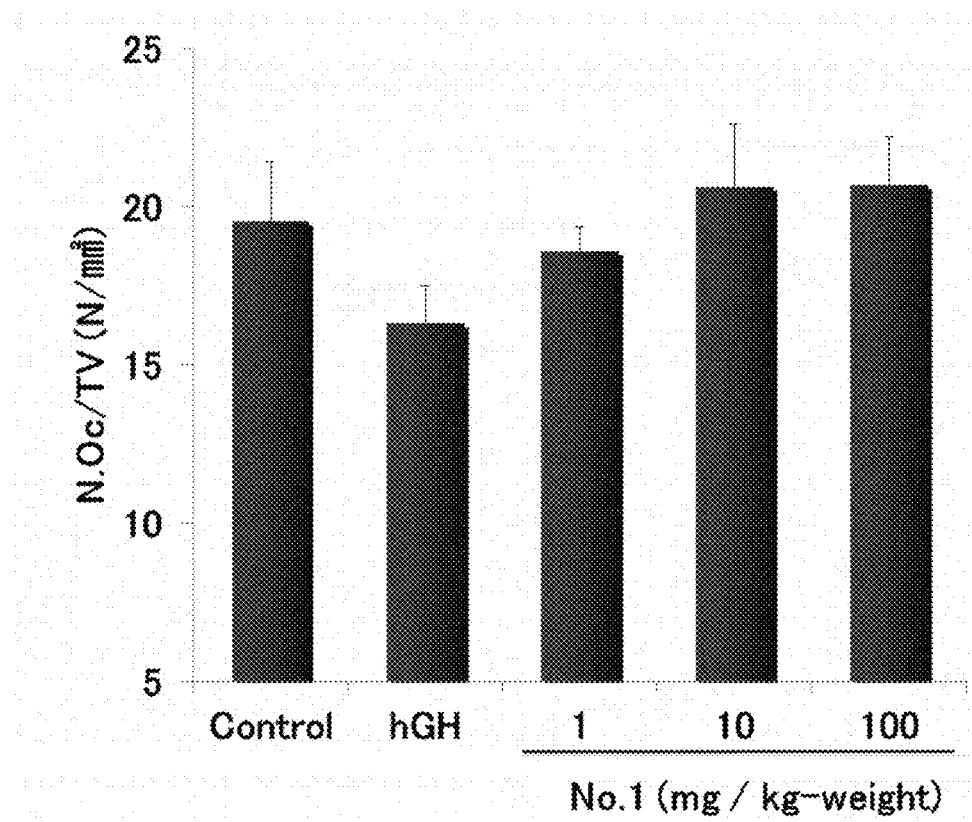
FIG. 23 is a graph showing the number of osteoclasts per unit bone surface of rats in synthetic peptide (No. 1) administration groups.

A significant increase in the calcification rate (mineral apposition rate) in the hGH and synthetic peptide No. 1 administration groups was observed as compared with the control group. The synthetic peptide No. 1 administration groups also showed a significant increase in the calcification rate at a dose of 10 mg/kg/day or more as compared with the hGH administration group (FIG. 18). The analysis of the secondary cancellous bone volume (bone volume/tissue volume (BV/TV)) showed that the synthetic peptide No. 1 administration group (10 mg/kg) had a higher secondary cancellous bone volume than the hGH administration group (FIG. 19). The synthetic peptide No. 1 administration groups also showed a higher percentage of the bone surface occupied by osteoblasts relative to the total bone surface (osteoblast surface/bone surface (Ob.S/BS)) and a larger number of osteoblasts per unit bone surface (number of osteoblasts/tissue volume (N.Ob/TV)) (FIGS. 20 and 21), but showed similar results to the control in terms of the percentage of the bone surface occupied by osteoclasts (osteoclast surface/bone surface (Oc.S/BS)) and the number of osteoclasts per unit bone surface (number of osteoclasts/tissue volume (N.Oc/TV)), revealing that the peptide does not affect osteoclasts (FIGS. 22 and 23). The results indicated that the increase in the calcification rate and the bone volume in the secondary cancellous bone in the synthetic peptide No. 1 administration groups was resulted from the increase in the number of osteoblasts.

The above results revealed that oral administration of the peptide of the present invention promotes calcification in the secondary cancellous bone and increases the bone formation rate.

Example 7: Study of Effect of Synthetic Peptides on Body Weight

Figure 24:
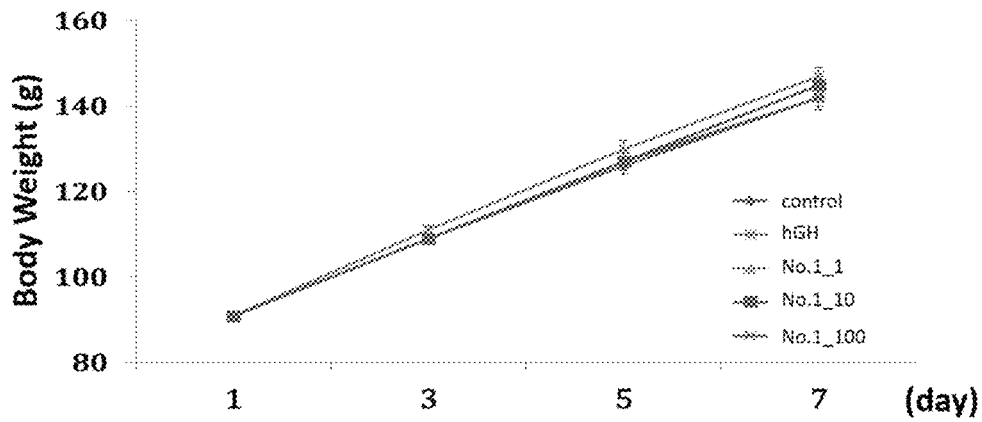
FIG. 24 is a graph showing the change in the body weight of rats with time in synthetic peptide (No. 1) administration groups.

The synthetic peptide No. 1 or water for injection (control) was administered to male Crlj:WI rats at the age of four weeks by oral gavage using a gastric tube once a day for seven days (n=10 in each group). The dosage of the synthetic peptide was 1, 10 or 100 mg/kg/day. As a positive control, human growth hormone (hGH) (Norditropin, Japan Standard Commodity Classification Number: 872412) was subcutaneously administered at 500 μg/kg/day once a day for seven days. The body weight was measured on days 1, 3, 5 and 7 of administration. No significant change in the body weight was observed in any group during the administration period (FIG. 24). The results indicated that seven-day continuous oral administration of the peptide of the present invention does not affect the body weight.

Example 8: Study of Promoting Effect of Synthetic Peptides on Production of Insulin-Like Growth Factor (IGF-1)

Figure 25:
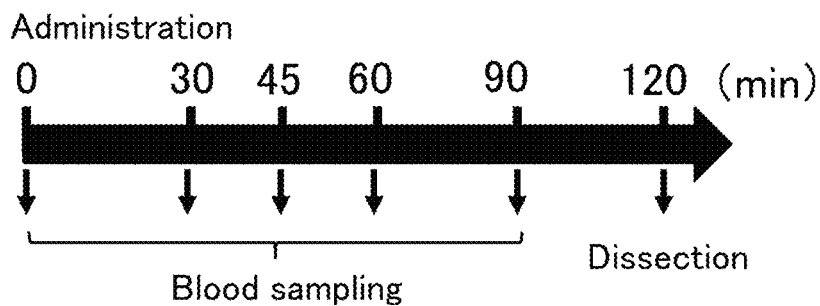
FIG. 25 shows the experimental protocol of Example 8.

The synthetic peptide No. 1 or No. 2 or water for injection (control) was orally administered as a single dose to male Wistar rats at the age of four weeks by using a gastric tube (n=6 in each group). The dosage of the synthetic peptide No. 1 or No. 2 was 10 mg/kg. The blood was collected from the tail before administration and 30, 45, 60 and 90 minutes after administration, and the serum was separated. At 120 minutes after administration, the whole blood was collected from the abdominal vena cava under anesthesia and the rats were euthanized (see FIG. 25). The concentration of IGF-1 in the serum was measured by ELISA (Mouse/Rat IGF-I Quantikine ELISA Kit (MG100), R&D Systems, Inc.).

Figure 26:
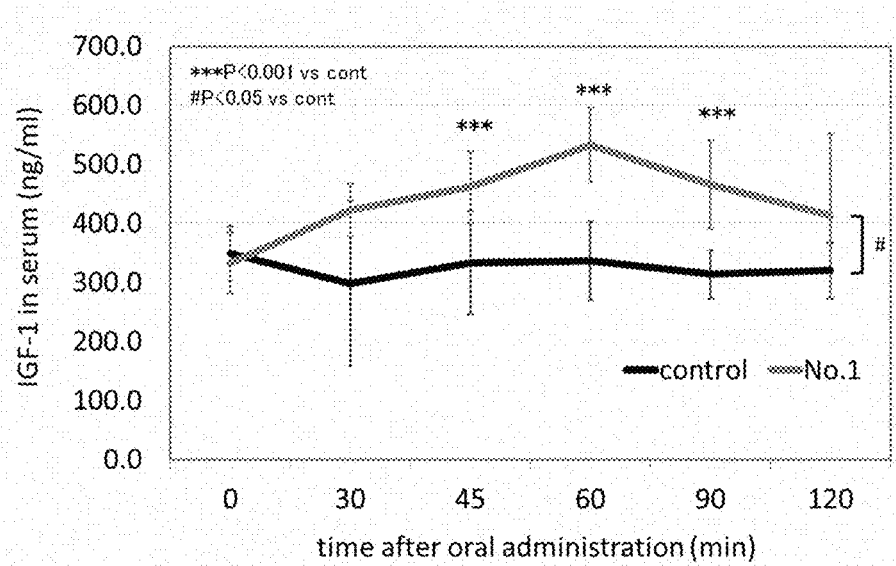
FIG. 26 is a graph showing the results of the time course measurement of the concentration of insulin-like growth factor (IGF-1) in the serum of rats in a single-dose synthetic peptide (No. 1) administration group.
Figure 27:
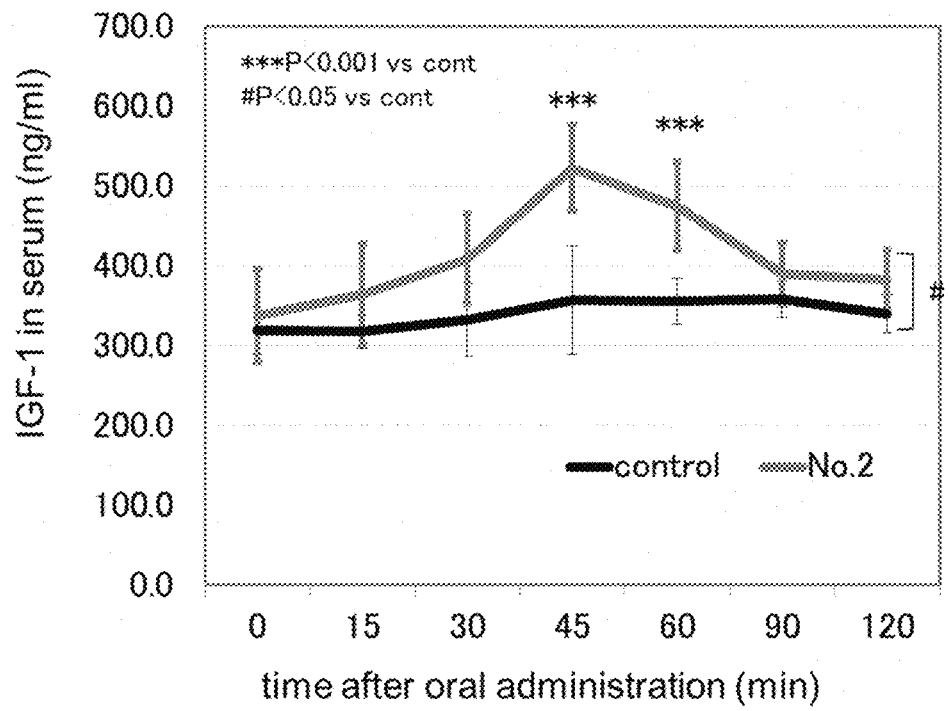
FIG. 27 is a graph showing the results of the time course measurement of the concentration of insulin-like growth factor (IGF-1) in the serum of rats in a single-dose synthetic peptide (No. 2) administration group.

The concentration of IGF-1 in the serum in the synthetic peptide No. 1 administration group was significantly higher than that of the control at 45, 60 and 90 minutes after administration. The concentration of IGF-1 in the serum in the synthetic peptide No. 2 administration group was significantly higher than that of the control at 45 and 60 minutes after administration (FIGS. 26 and 27).

Figure 28:
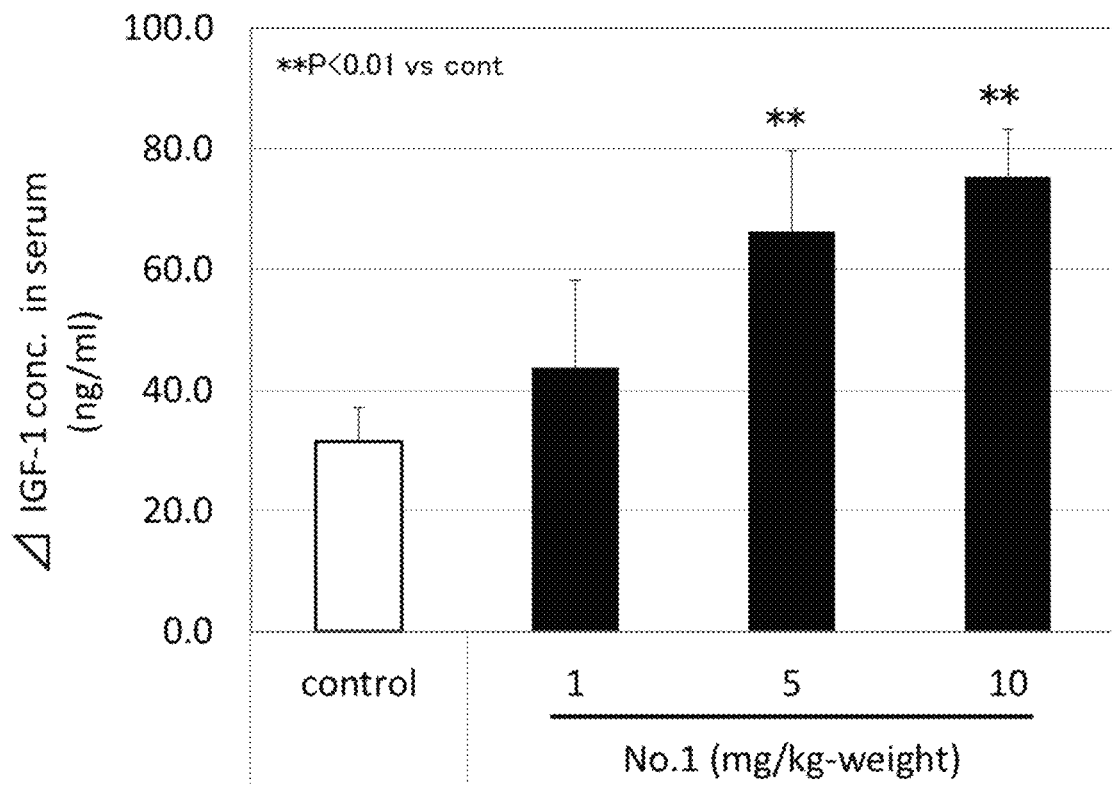
FIG. 28 is a graph showing the concentration of insulin-like growth factor (IGF-1) in the serum of rats in single-dose synthetic peptide (No. 1) administration groups.
Figure 29:
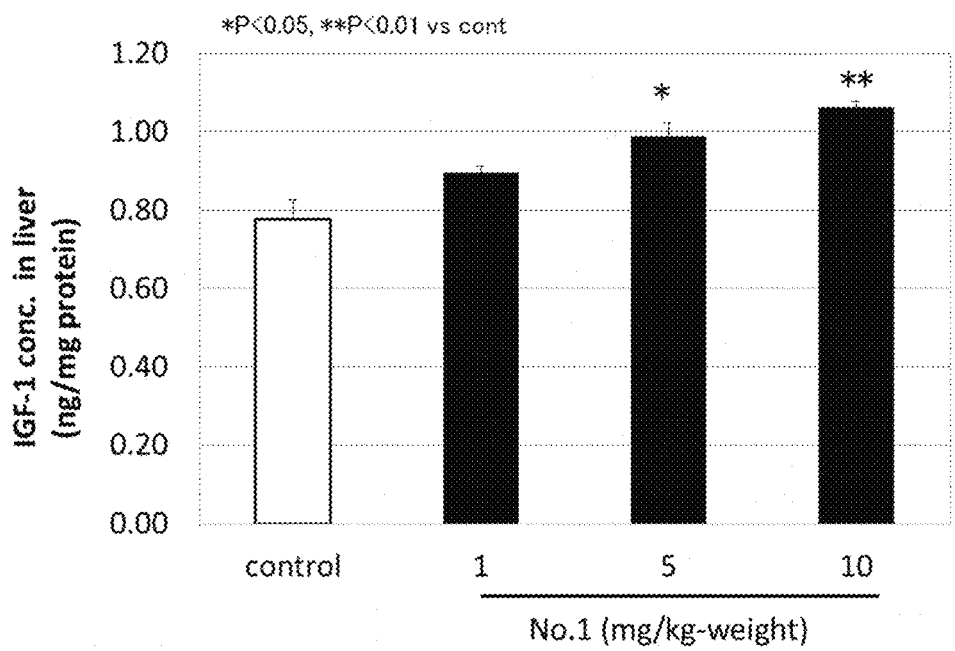
FIG. 29 is a graph showing the concentration of insulin-like growth factor (IGF-1) in the liver of rats in single-dose synthetic peptide (No. 1) administration groups.

The concentration dependence of the synthetic peptides was examined. The synthetic peptide No. 1 was orally administered as a single dose of 1, 5 or 10 mg/kg (n=6 in each group). At 60 minutes after administration, the rats were euthanized under anesthesia, and the liver was harvested. The concentration of IGF-1 in the serum and liver was measured. For the serum IGF-1 concentration, the difference (Δ value) before and after administration was also determined. The concentration of IGF-1 in the serum and liver was significantly higher in the synthetic peptide No. 1 administration groups than in the control group, and increased in a dose-dependent manner (FIGS. 28 and 29).

Figure 30:
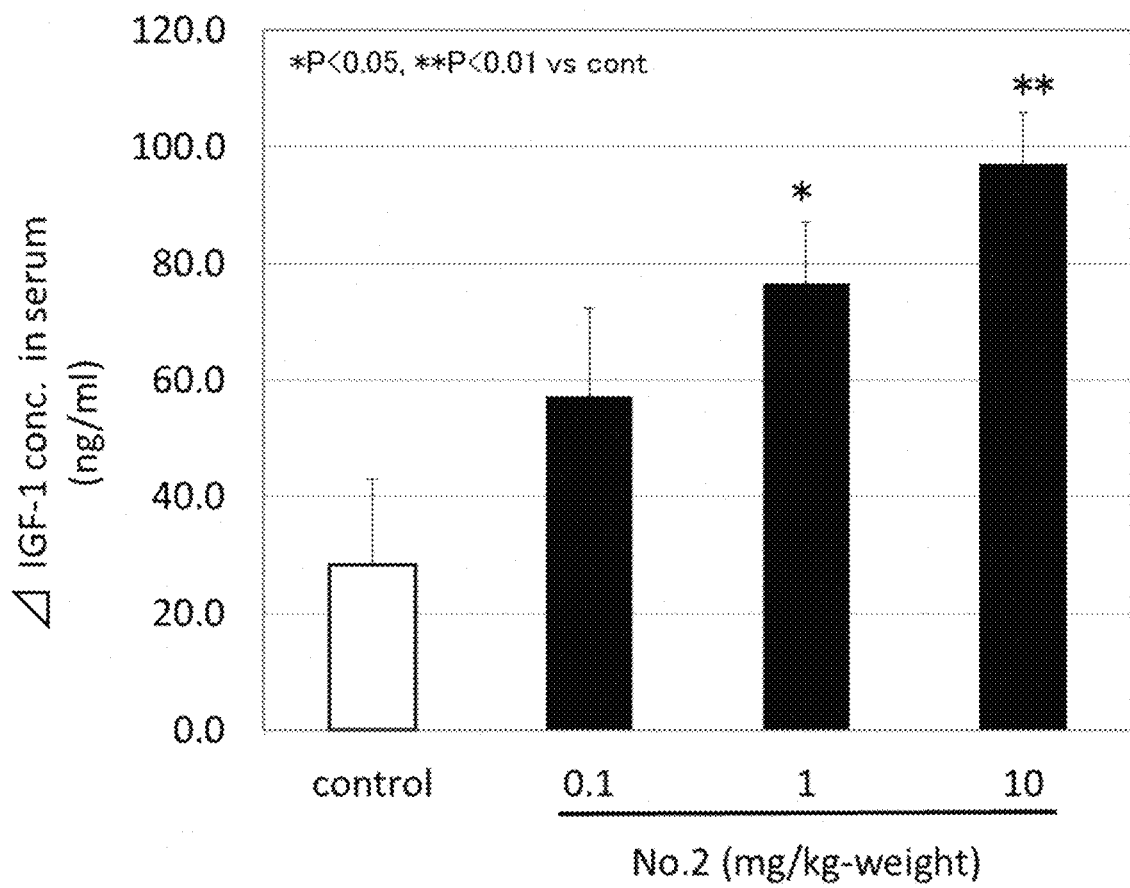
FIG. 30 is a graph showing the concentration of insulin-like growth factor (IGF-1) in the serum of rats in single-dose synthetic peptide (No. 2) administration groups.
Figure 31:
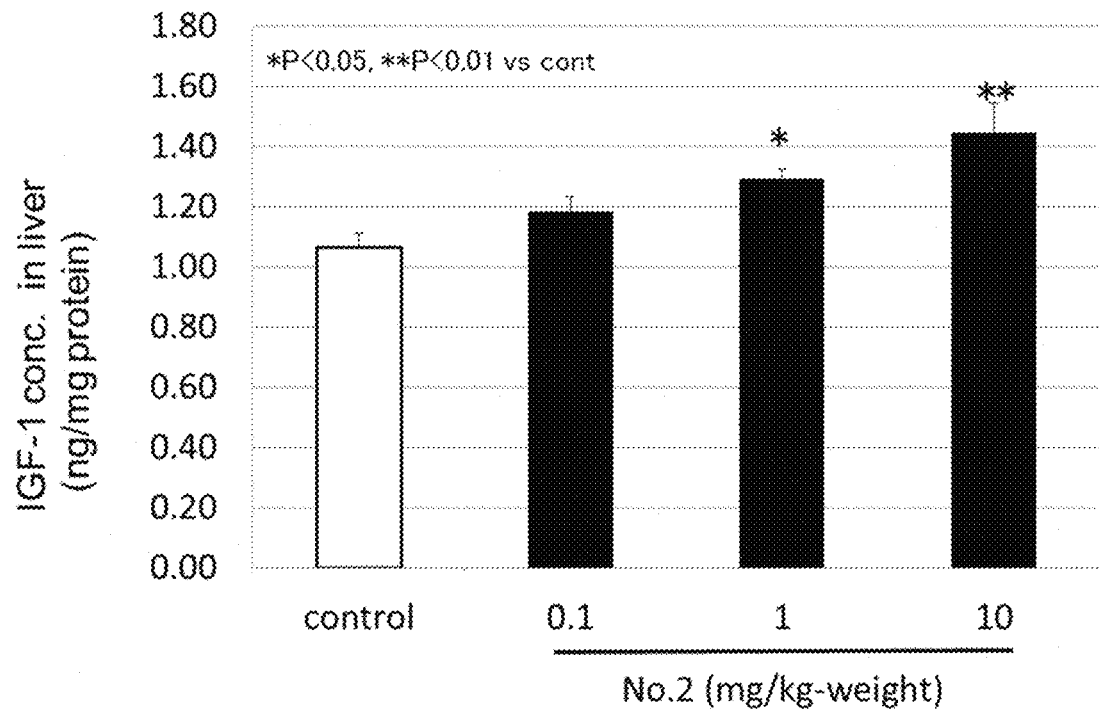
FIG. 31 is a graph showing the concentration of insulin-like growth factor (IGF-1) in the liver of rats in single-dose synthetic peptide (No. 2) administration groups.

The synthetic peptide No. 2 was orally administered to the rats as a single dose of 0.1, 1 or 10 mg/kg (n=6 in each group). At 45 minutes after administration, the rats were euthanized under anesthesia, and the liver was harvested. The concentration of IGF-1 in the serum and liver was measured. For the serum IGF-1 concentration, the difference (Δ value) before and after administration was also determined. The concentration of IGF-1 in the serum and liver was significantly higher in the synthetic peptide No. 2 administration groups than in the control group, and increased in a dose-dependent manner (FIGS. 30 and 31).

IGF-1 is produced in the liver and involved in bone formation. Taken together, the peptides of the present invention promote IGF-1 production in the body, thereby promoting osteogenesis.

The results indicated that oral administration of the peptides Nos. 1 and 2 of the present invention promotes IGF-1 production in the body.

Example 9: Study of Promoting Effect of Synthetic Peptide Administration on Production of IGF-1

The synthetic peptide No. 2, a peptide consisting of a reverse sequence of the peptide No. 2 (SEQ ID NO: 3; herein also called R-No. 2), constituent amino acids of the synthetic peptide No. 2 (herein also called AA), or water for injection (control) was orally administered as a single dose to male Wistar rats at the age of four weeks by using a gastric tube (n=6 in each group). The dosage of the synthetic peptide, the reverse sequence peptide and the constituent amino acids was 10 mg/kg. At 45 minutes after administration, the rats were euthanized under anesthesia, and the liver was harvested. The concentration of IGF-1 in the serum and liver was measured by ELISA (Mouse/Rat IGF-I Quantikine ELISA Kit (MG100), R&D Systems, Inc.). For the serum IGF-1 concentration, the difference (Δ value) before and after administration was also determined.

Figure 32:
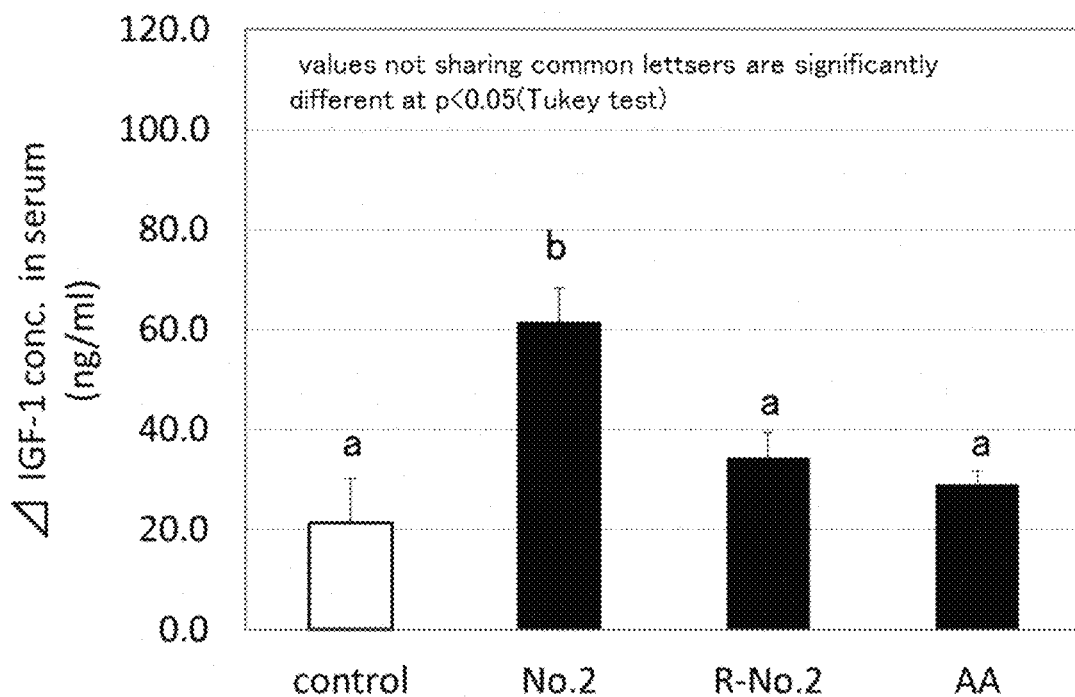
FIG. 32 is a graph showing the concentration of insulin-like growth factor (IGF-1) in the serum of rats in three groups with single-dose administration of any one of the following peptides: a synthetic peptide (No. 2), a reverse sequence of the synthetic peptide (No. 2) and constituent amino acids of the synthetic peptide (No. 2).
Figure 33:
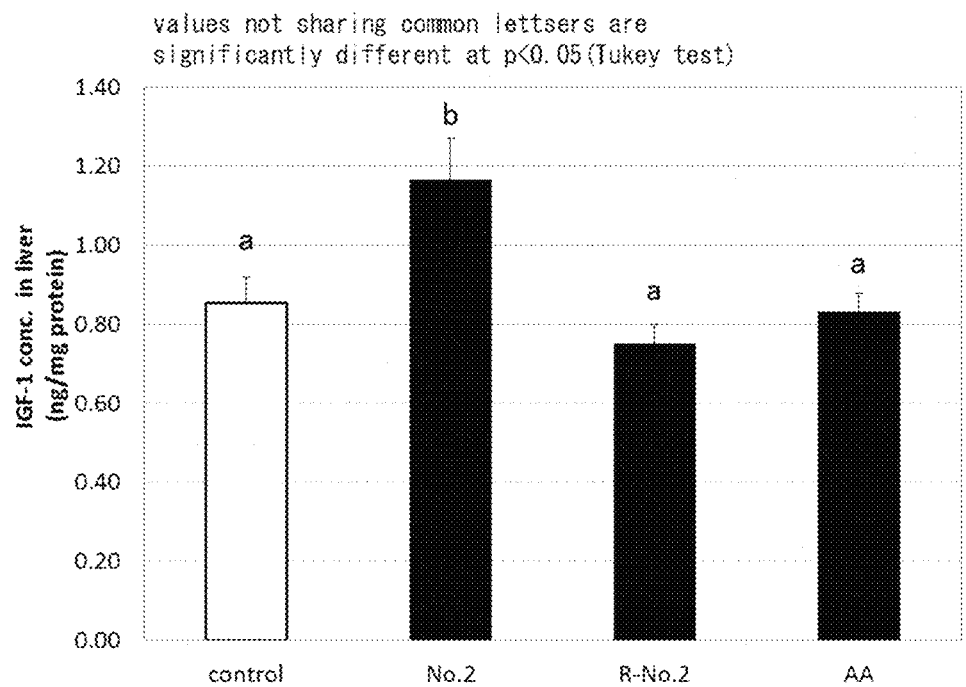
FIG. 33 is a graph showing the concentration of insulin-like growth factor (IGF-1) in the liver of rats in three groups with single-dose administration of any one of the following peptides: a synthetic peptide (No. 2), a reverse sequence of the synthetic peptide (No. 2) and constituent amino acids of the synthetic peptide (No. 2).

The concentration of IGF-1 in the serum and liver was significantly higher only in the synthetic peptide No. 2 administration group (FIGS. 32 and 33). The results indicated that the IGF-1 production-promoting effect of the synthetic peptide No. 2 of the present invention is specific to the peptide sequence.

Example 10: Study of Effect of Synthetic Peptide Administration on Parathyroid Hormone Concentration The synthetic peptide No. 1 or water for injection (control) was orally administered as a single dose to male Wistar rats at the age of four weeks by using a gastric tube (n=6 in each group). The dosage of the synthetic peptide was 10 mg/kg/day. The blood was collected from the tail before administration and 30, 45, 60 and 90 minutes after administration, and the serum was separated. At 120 minutes after administration, the whole blood was collected from the abdominal vena cava under anesthesia and the rats were euthanized. The concentration of parathyroid hormone (PTH) in the serum was measured by ELISA (Enzyme-linked Immunosorbent Assay Kit for Parathyroid Hormone (PTH), Uscn Life Science Inc.).

Figure 34:
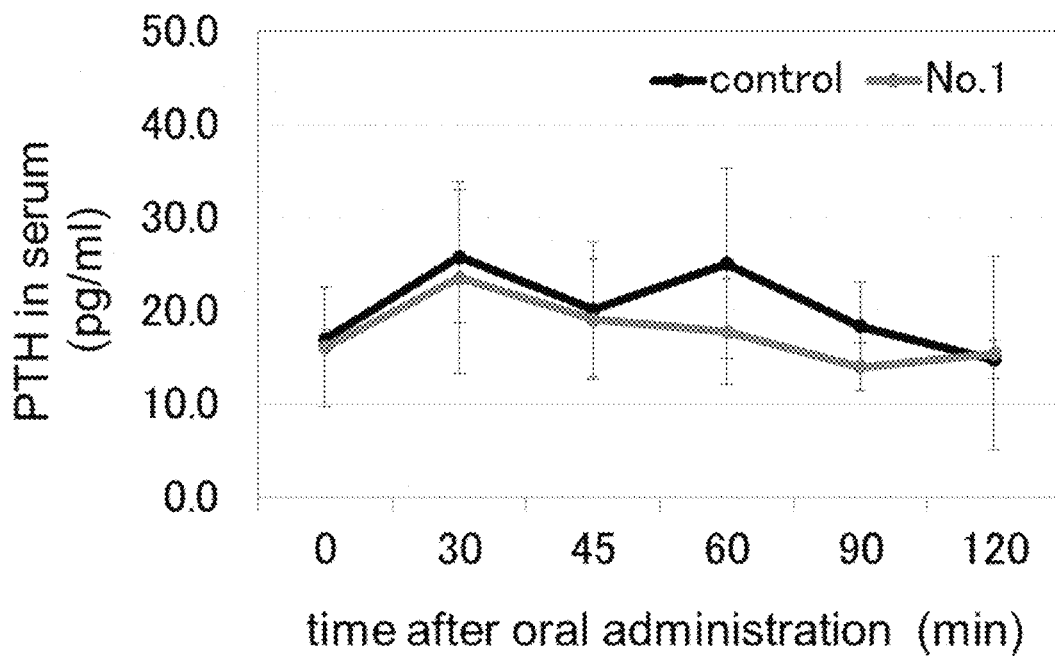
FIG. 34 is a graph showing the results of time course measurement of the concentration of parathyroid hormone (PTH) in the plasma of rats in a single-dose synthetic peptide (No. 1) administration group.

No significant difference in the serum PTH concentration was observed between the synthetic peptide No. 1 administration group and the control group (FIG. 34). PTH is known to be involved in bone metabolism, and continuous administration of PTH results in promotion of bone resorption, whereas intermittent administration of PTH results in promotion of bone formation. Currently available PTH medicines are osteogenesis-promoting agents utilizing these characteristics. The synthetic peptide of the present invention does not affect the PTH concentration in the serum, suggesting that the synthetic peptide promotes osteogenesis via a different mechanism of action from currently available PTH drugs.

Example 11: Study of Digestive Juice Resistance of Synthetic Peptides

Figure 35:
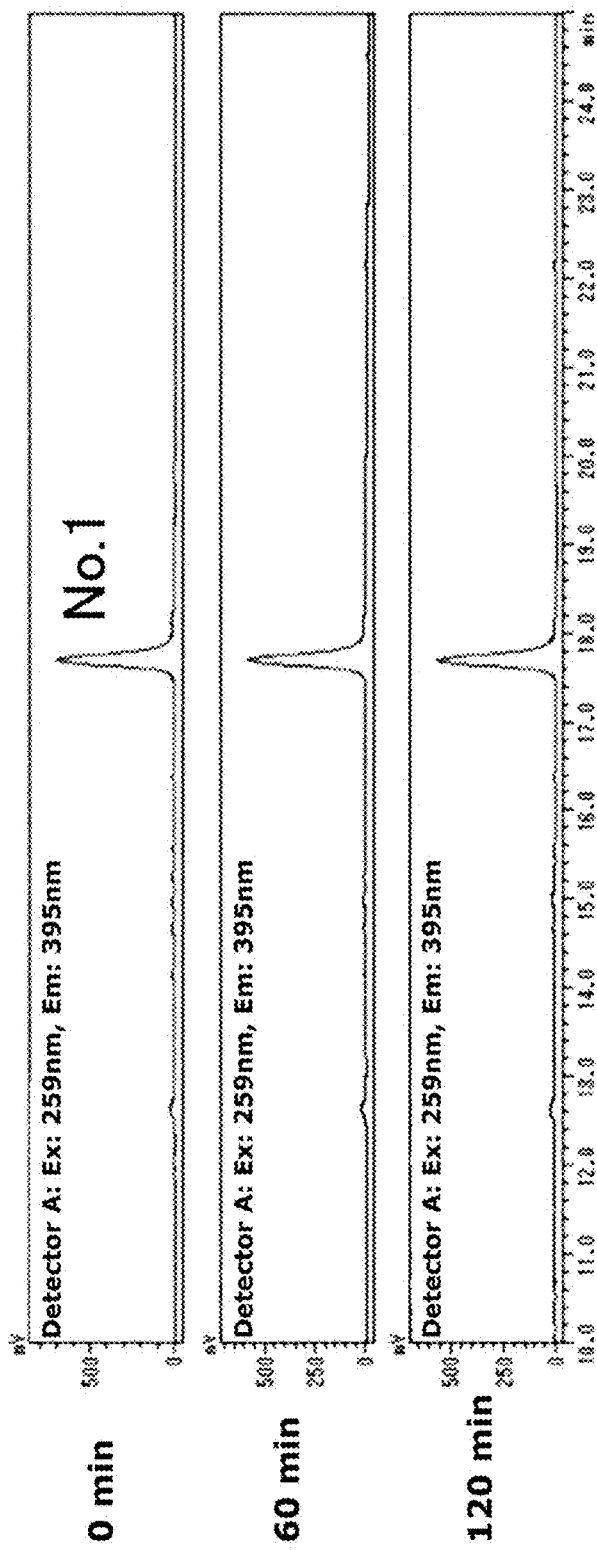
FIG. 35 is a graph showing the results of a digestion test of a synthetic peptide (No. 1) using artificial gastric juice (0.2% NaCl, 0.32% pepsin, 2.4% diluted hydrochloric acid, adjusted to pH 3.0).

A test using artificial gastric juice was performed on the synthetic peptide No. 1. Ten milligrams of the synthetic peptide No. 1 was dissolved in 1 mL of artificial gastric juice (0.2% NaCl, 0.32% pepsin, 2.4% diluted hydrochloric acid, adjusted to pH 3.0), and the mixture was allowed to react under shaking at 37° C. Samples were collected before the reaction and 60 and 120 minutes after the reaction, and subjected to HPLC [column: ODS column (size: diameter 46 mm×500 mm, SHIMADZU); mobile phase: (A) 0.05% TFA, (B) 90% acetonitrile/0.05% TFA; gradient: 2% B (0 min), 20% B (50 min), 100% B (50.1 min), 100% B (55 min); detection: UV 215 nm] to examine whether the synthetic peptide No. 1 was decomposed by the gastric juice (resistance to the gastric juice). The synthetic peptide No. 1 was not decomposed even when reacted in the artificial gastric juice for 60 and 120 minutes, showing high resistance (FIG. 35).

Figure 36:
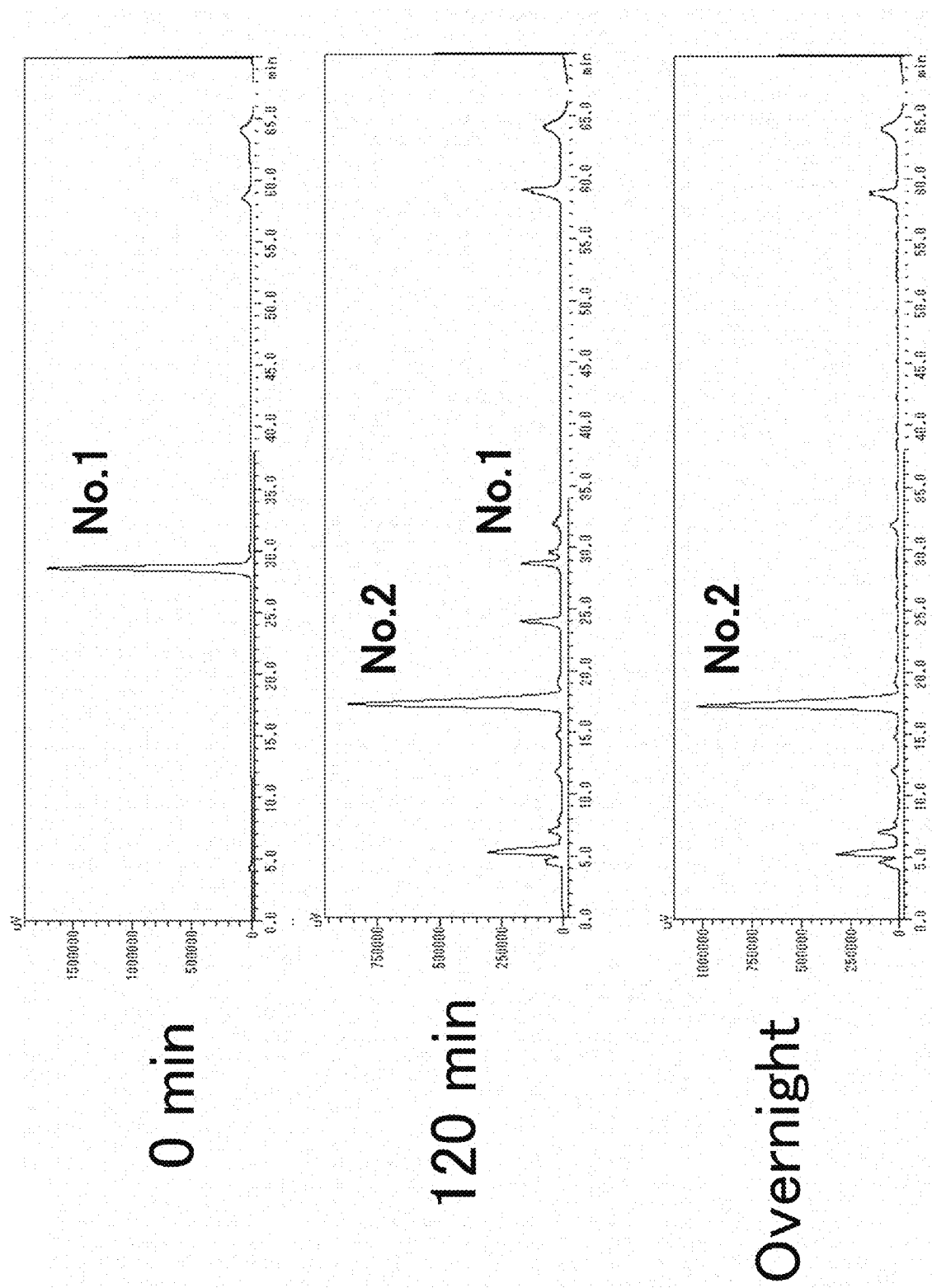
FIG. 36 is a graph showing the results of a digestion test of a synthetic peptide (No. 1) using artificial intestinal juice (0.34% $KH_2PO_4$, 0.36% $Na_2HPO_4$, 1% pancreatin, adjusted to pH 6.8).

Ten milligrams of the synthetic peptide No. 1 was dissolved in 1 mL of artificial intestinal juice (0.34% $KH_2PO_4$, 0.36% $Na_2HPO_4$, 1% pancreatin, adjusted to pH 6.8), and the mixture was allowed to react under shaking at 37° C. Samples were collected before the reaction, 120 minutes after the reaction and after overnight reaction, and subjected to HPLC [column: ODS column (size: diameter 46 mm×500 mm, SHIMADZU); mobile phase: (A) 0.05% TFA, (B) 90% acetonitrile/0.05% TFA; gradient: 2% B (0 min), 20% B (50 min), 100% B (50.1 min), 100% B (55 min); detection: UV 215 nm] to examine whether the synthetic peptide No. 1 was decomposed by the intestinal juice (resistance to the intestinal juice). The synthetic peptide No. 1 was decomposed in the artificial intestinal juice, and in the end, totally decomposed into a peptide having the sequence of the synthetic peptide No. 2 (FIG. 36).

The results indicated that, when the synthetic peptide No. 1 of the present invention is ingested, the peptide is decomposed into the synthetic peptide No. 2 in the digestive tract.

Example 12: Study of Absorption of Synthetic Peptides into the Body

The synthetic peptide No. 1 was labeled with Cyanine3 (Cy3) NHS ester (Lumiprobe Corporation, Cat #: 61020). Twenty milligrams of the synthetic peptide No. 1 was dissolved in 9.2 mL of 0.1 M $NaHCO_3$ (pH 8.3), and 9 mL of the peptide solution was mixed with 1 mL of Cy3 NHS ester solution in dimethylsulfoxide (10 mg/mL). The mixture was left to stand at room temperature with protection from light for 4 hours, and purified on a G-10 gel-filtration column (Sephadex G-10, GE Healthcare Ltd.). The solvent was removed by lyophilization to give Cy3-labeled synthetic peptide No. 1. The Cy3-labeled synthetic peptide No. 1 was orally administered as a single dose to male ddY mice at the age of seven weeks. The dosage of the Cy3-labeled synthetic peptide No. 1 was 100 mg/kg. At 15 minutes after administration, the blood was collected from the portal vein under anesthesia and the mice were euthanized. The stomach, small intestine, liver, kidney, heart, lung, brain and femur were harvested, and each tissue was homogenized. The serum was separated from the portal vein blood. The homogenized tissue and the serum were subjected to HPLC [column: ODS column (size: diameter 46 mm×500 mm, SHIMADZU); mobile phase: (A) 0.05% TFA, (B) 90% acetonitrile/0.05% TFA; gradient: 2% B (0 min), 20% B (50 min), 100% B (50.1 min), 100% B (55 min); detection: UV 215 nm] to examine whether the Cy3-labeled synthetic peptide No. 1 was detected from the living body.

Figure 37:
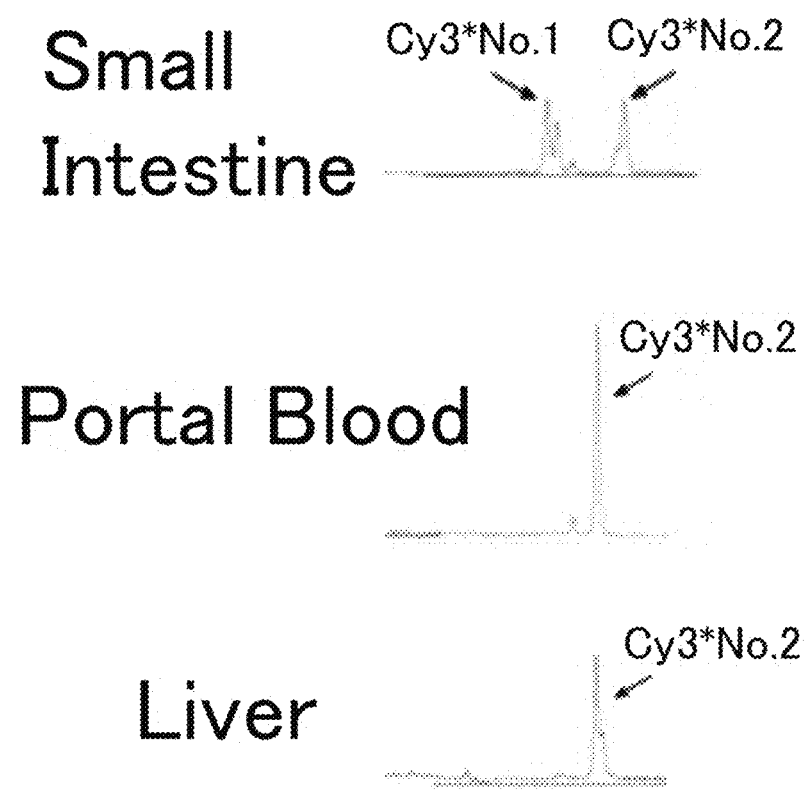
FIG. 37 is a graph showing the measurement results of the absorption of a synthetic peptide (No. 1) labeled with a fluorochrome (Cy3) into the body of mice in a single-dose Cy3-labeled synthetic peptide (No. 1) administration group.

A portion of the Cy3-labeled synthetic peptide No. 1 was decomposed in the small intestine, and both the Cy3-labeled synthetic peptides Nos. 1 and 2 were detected in the small intestine. In the portal vein blood and the liver, only the Cy3-labeled synthetic peptide No. 2 was detected (FIG. 37). The results indicated that the synthetic peptide No. 1 of the present invention is decomposed into a peptide having the sequence of the synthetic peptide No. 2 in the small intestine, which is then absorbed from the small intestine and is transported to the liver via the blood. In summary, the orally ingested synthetic peptide No. 1 is metabolized into the synthetic peptide No. 2 and reaches the digestive tract, whereas the orally ingested synthetic peptide No. 2 reaches the digestive tract while maintaining the structure. The synthetic peptide No. 2 has a small molecular weight, and is thus rapidly and efficiently absorbed from the digestive tract. The results suggested that both the synthetic peptides Nos. 1 and 2, when orally ingested, effectively exert their effects.

The present invention is not limited to each of the embodiments and Examples as described above, and various modifications are possible within the scope of the claims. Embodiments obtainable by appropriately combining the technical means disclosed in different embodiments of the present invention are also included in the technical scope of the present invention. The contents of the scientific literature and the patent literature cited herein are hereby incorporated by reference in their entirety.

The invention claimed is:

1. A method for treating osteogenesis imperfecta in a mammal, the method comprising administering, to the mammal, an effective amount of a peptide consisting of the amino acid sequence Val-Asn-Pro-Glu (SEQ ID NO: 2).

2. The method according to claim 1, wherein the peptide prevents a bone fracture and/or promotes the healing of a bone fracture in the mammal.

3. The method according to claim 1, wherein the peptide is administered orally.

4. The method according to claim 1, comprising administering the peptide simultaneously or sequentially with a compound having an inhibitory effect on osteoclasts or with a bisphosphonate.

5. A method for treating osteoporosis in a mammal, the method comprising administering, to the mammal, an effective amount of a peptide consisting of the amino acid sequence Val-Asn-Pro-Glu (SEQ ID NO: 2).

6. The method according to claim 5, wherein the peptide prevents a bone fracture and/or promotes the healing of a bone fracture in the mammal.

7. The method according to claim 5, wherein the peptide is administered orally.

8. The method according to claim 5, comprising administering the peptide simultaneously or sequentially with a compound having an inhibitory effect on osteoclasts or with a bisphosphonate.

9. A method for treating osteoarthritis in a mammal, the method comprising administering, to the mammal, an effective amount of a peptide consisting of the amino acid sequence Val-Asn-Pro-Glu (SEQ ID NO: 2).

10. The method according to claim 9, wherein the peptide is administered orally.

* * * * *